US010238520B2

(12) United States Patent
Summit et al.

(10) Patent No.: US 10,238,520 B2
(45) Date of Patent: Mar. 26, 2019

(54) ADJUSTABLE BRACE

(71) Applicants: Scott Summit, Mill Valley, CA (US);
Kenneth B Trauner, San Francisco, CA (US)

(72) Inventors: Scott Summit, Mill Valley, CA (US);
Kenneth B Trauner, San Francisco, CA (US)

(73) Assignee: 3D SYSTEMS, INC., Rock Hill, SC (US)

( * ) Notice: Subject to any disclaimer, the term of this patent is extended or adjusted under 35 U.S.C. 154(b) by 1087 days.

(21) Appl. No.: 14/255,801

(22) Filed: Apr. 17, 2014

(65) Prior Publication Data
US 2014/0228725 A1 Aug. 14, 2014

Related U.S. Application Data

(63) Continuation-in-part of application No. 13/214,096, filed on Aug. 19, 2011, now abandoned, which is a
(Continued)

(51) Int. Cl.
A61F 5/00 (2006.01)
A61F 5/01 (2006.01)
A61F 5/02 (2006.01)

(52) U.S. Cl.
CPC ............ A61F 5/0102 (2013.01); A61F 5/01 (2013.01); A61F 5/013 (2013.01); A61F 5/0123 (2013.01);
(Continued)

(58) Field of Classification Search
CPC .......... A61F 5/0102; A61F 5/01; A61F 5/013; A61F 5/02; A61F 2005/0132; A61F 5/10;
(Continued)

(56) References Cited

U.S. PATENT DOCUMENTS 2,318,864 A 2/1940 Jackson
2,692,594 A 10/1954 Kelly
(Continued)

FOREIGN PATENT DOCUMENTS

JP H111999318962 11/1999
JP 2000-502584 3/2000
(Continued)

OTHER PUBLICATIONS

English Translation of China's First Office Action for Chinese Application No. 201180040807.2 dated May 12, 2014 (8 pages).
(Continued)

Primary Examiner — Victoria J Hicks
(74) Attorney, Agent, or Firm — Staniford Tomita LLP

(57) ABSTRACT

An adjustable brace includes a first portion for supporting one surface of a patient and a plurality of adjustable portions that allow the internal cross section of the brace to be adjusted. When a limb is injured, a patient may have a swollen limb and the adjustable brace can be set to a large cross section. As the limb heals, the swelling decreases and the limb cross section also decreases due to atrophy. The adjustable couplings are adjusted to reduce the cross section to properly fit the limb of the patient and provide proper protection and support during the healing process.

13 Claims, 23 Drawing Sheets

Related U.S. Application Data continuation-in-part of application No. 12/820,968, filed on Jun. 22, 2010, now abandoned, which is a continuation-in-part of application No. 12/615,196, filed on Nov. 9, 2009, now Pat. No. 8,005,651.

(60) Provisional application No. 61/112,751, filed on Nov. 9, 2008, provisional application No. 61/168,183, filed on Apr. 9, 2009, provisional application No. 61/185,781, filed on Jun. 10, 2009.

(52) U.S. Cl.
 CPC ........ *A61F 5/02* (2013.01); *A61F 2005/0132* (2013.01)

(58) Field of Classification Search
 CPC ...... A61F 5/05; A61F 5/05841; A61F 5/0585; A61F 5/05858; A61F 5/05866; A61F 5/05875; A61F 5/058; A61F 5/055; A61F 5/00; A61F 5/024; A61F 5/028
 USPC .... 602/12; 24/483, 484, 298, 634, 652, 285, 24/300, 657, 282, 301, 656, 284, 302, 24/286, 635, 629, 648; 403/26, 167, 168, 403/221, 222, 223, 220, 292, 293, 296
 See application file for complete search history.

(56) References Cited

U.S. PATENT DOCUMENTS

| | | | |
|---|---|---|---|
| 2,980,110 | A | 4/1961 | Brumfield et al. |
| 3,093,131 | A | 6/1963 | Kashyap |
| 3,298,366 | A * | 1/1967 | Moore .................. A61F 13/148 450/155 |
| 3,953,900 | A | 5/1976 | Thompson |
| 4,776,327 | A | 10/1988 | Russell |
| 4,807,605 | A | 2/1989 | Mattingly |
| 4,827,916 | A | 5/1989 | Kosova |
| 4,898,160 | A | 2/1990 | Brownlee |
| 5,014,689 | A | 5/1991 | Meunchen et al. |
| 5,443,510 | A | 8/1995 | Shetty et al. |
| 5,662,594 | A | 9/1997 | Rosenblatt |
| 5,695,452 | A | 12/1997 | Grim |
| 5,713,837 | A | 2/1998 | Grim et al. |
| 5,741,215 | A | 4/1998 | D'Urso |
| 5,768,134 | A | 6/1998 | Swaelens et al. |
| 5,880,964 | A | 3/1999 | Schall et al. |
| 5,888,216 | A | 3/1999 | Haberman |
| 5,857,987 | A | 6/1999 | Habermeyer |
| 5,911,126 | A | 6/1999 | Massen |
| 6,427,695 | B1 | 8/2002 | Zanetti et al. |
| 6,540,706 | B1 | 4/2003 | Manspaizer |
| 6,572,571 | B2 | 6/2003 | Lowe |
| 6,597,965 | B2 | 7/2003 | Graves et al. |
| 6,613,006 | B1 | 9/2003 | Asherman |
| 6,725,118 | B1 | 4/2004 | Fried et al. |
| 6,726,641 | B2 | 4/2004 | Chiang et al. |
| 6,899,689 | B1 | 5/2005 | Modglin |
| 6,968,246 | B2 | 11/2005 | Watson |
| 7,058,471 | B2 | 6/2006 | Watanabe |
| 7,127,101 | B2 | 10/2006 | Littlefield et al. |
| 7,329,232 | B2 * | 2/2008 | Lipshaw ................ A61F 13/06 128/845 |
| 7,340,316 | B2 | 3/2008 | Spaeth et al. |
| 7,896,827 | B2 | 3/2011 | Ingimundarson et al. |
| 8,005,651 | B2 | 8/2011 | Summit et al. |
| 2002/0016631 | A1 | 2/2002 | Marchitto et al. |
| 2002/0026135 | A1* | 2/2002 | Lowe .................... A61F 5/0585 602/5 |
| 2002/0068890 | A1 | 6/2002 | Schwenn |
| 2003/0032906 | A1* | 2/2003 | Narula ................ A61F 5/05841 602/5 |
| 2003/0065259 | A1 | 4/2003 | Gatena et al. |
| 2004/0019266 | A1 | 1/2004 | Marciante et al. |
| 2004/0068337 | A1 | 4/2004 | Watson et al. |
| 2004/0162511 | A1 | 4/2004 | Barberio |
| 2004/0230149 | A1 | 11/2004 | Littlefield et al. |
| 2004/0236424 | A1 | 11/2004 | Berez et al. |
| 2004/0260402 | A1 | 12/2004 | Baldini et al. |
| 2005/0015172 | A1 | 1/2005 | Fried |
| 2005/0016631 | A1 | 1/2005 | Marchitto et al. |
| 2005/0043835 | A1 | 2/2005 | Christensen |
| 2005/0054960 | A1 | 3/2005 | Telles |
| 2005/0061332 | A1 | 3/2005 | Greenawalt et al. |
| 2005/0065458 | A1 | 3/2005 | Kim |
| 2006/0140463 | A1 | 6/2006 | Rutschmann |
| 2006/0161267 | A1 | 7/2006 | Clausen |
| 2007/0016323 | A1 | 1/2007 | Fried |
| 2007/0225630 | A1 | 9/2007 | Wyatt et al. |
| 2008/0120756 | A1 | 5/2008 | Shephard |
| 2008/0294083 | A1 | 11/2008 | Chang et al. |
| 2008/0319362 | A1 | 12/2008 | Joseph |
| 2009/0254015 | A1 | 10/2009 | Segal et al. |
| 2009/0306801 | A1 | 12/2009 | Sivak |
| 2010/0137770 | A1 | 6/2010 | Ingimundarson et al. |
| 2010/0138193 | A1 | 6/2010 | Summit |
| 2010/0298750 | A1 | 11/2010 | Chiang et al. |

FOREIGN PATENT DOCUMENTS

| | | |
|---|---|---|
| JP | 2000-592854 | 3/2000 |
| JP | 2006-513482 | 4/2006 |
| JP | 2007068855 | 3/2007 |
| WO | 97/24085 | 7/1997 |
| WO | 2010/054341 | 5/2010 |
| WO | 2010-054341 | 5/2010 |
| WO | 2010/099130 | 9/2010 |

OTHER PUBLICATIONS

English Translation of Japan's First Office Action for Japanese Application No. 2012-538868 dated Jun. 6, 2014 (3 pages).
English translation of Japan's First Office Action dated Mar. 24, 2015 (3 pages).
English translation of KIPO's Notice of Preliminary Rejection of Korea Patent Application No. 10-2011-7013219 (3 pages).
English translation of Chinese First Office Action for Chinese Patent Application No. 201280040486.0 dated Mar. 9, 2015 (5 pages).
English translation of Chinese Third Office Action for Chinese Patent Application No. 201080060735.3 dated Aug. 4, 2015 (3 pages).
Canadian Office Action for Canadian Patent Application No. 2740797 dated Aug. 31, 2015 (3 pages).
European Search Report for European Patent Application No. 12825770.6 dated Sep. 3, 2015 (10 pages).
English translation of China's First Second Action for Chinese Application No. 201080060735.3 dated Apr. 1, 2014 (5 pages).
English translation of Korea's Second Office Action for Korea Patent Application No. 10-2014-7003756 (4 pages).
European Communication for European Patent Application No. 09825572.2 dated Aug. 1, 2016 (8 pages).
Vijay Kumar et al.: "Rapid Design and Prototyping of Customized Rehabilitation Aids", Communications of the ACM, vol. 39, No. 2, Feb. 28, 1996, pp. 55-61; ISSN: 0001-0782, DOI: 10.1145/230798. 230804.
International Search Report and Written Opinion for PCT Application No. PCT/US2010/055793 dated Jan. 5, 2011 (Jan. 5, 2011).
International Search Report for PCT/US2011/041515 dated Oct. 28, 2011 (Oct. 28, 2011).
International Search Report for PCT/US2012/051612 dated Oct. 26, 2012 (Oct. 26, 2012).
English translation of China's First Office Action for Chinese Application No. 200980144730.6 dated Nov. 28, 2012 (16 pages).
English translation of China's First Second Action for Chinese Application No. 200980144730.6 dated Aug. 12, 2013 (3 pages).
D. Fortin et al., "A 3D Visulatization tool for the design and customization of spinal braces," 2007, Computerized Medical Imaging and Graphics, vol. 31, pp. 614-624.

(56) References Cited

OTHER PUBLICATIONS

Alyssa Q. Caddle et al., "Design of Patient-Specific Ankle-Foot Orthotics," Nov. 5, 2007, Northeastern University, 149 pages.
F. Bemajdoub et al., "Computer aided design of scoliosis braces," 1992, 14th Annual International Conference of the IEEE Engineering in Biology Society, pp. 2068-2069.
P. Abellard et al., "Developpement d'une methode de reconstruction 3D du tronc d'un scoliotique par imagerie stereoscopique," 1993, GRETSI, Group d'Etudes du Traitement du Signal et des images, pp. 1299-1302.
J. Cottalorda et al., "Traitement orthopedique de la scoliose: nouvelie technique de prise d'empreinte par procede optique," 1997, Archives de Pediatrie, vol. 4, issue 5, pp. 464-467.
Phip Treleaven et al., "3D body scanning and healthcare applications," 2007, Computer, Jul. 2007, pp. 28-34.
English translation of China's Second Office Action dated Mar. 20, 2015 (7 pages).

\* cited by examiner

ADJUSTABLE BRACE

CROSS REFERENCE TO RELATED APPLICATIONS

This application is a continuation-in-part of U.S. patent application Ser. No. 13/214,096, Adjustable Brace" filed Aug. 19, 2011 which is a continuation-in-part of U.S. patent application Ser. No. 12/820,968, "Modular Custom Braces, Casts And Devices And Methods For Designing And Fabricating" filed Jun. 22, 2010 which is a continuation-in-part of U.S. patent application Ser. No. 12/615,196, now U.S. Pat. No. 8,005,651, "Custom Braces, Casts and Devices And Methods For Designing And Fabricating" filed Nov. 9, 2009 which claims priority to U.S. Provisional Patent Application No. 61/112,751, "Brace And Cast" filed on Nov. 9, 2008, U.S. Provisional Patent Application No. 61/168,183, "Orthopedic Braces" filed in Apr. 9, 2009, and U.S. Provisional Patent Application No. 61/185,781, "Bespoke Fracture Brace" filed in Jun. 10, 2009. This application also claims priority to U.S. Provisional Patent Application No. 61/375,699, "Adjustable Brace" filed Aug. 20, 2010. The contents of U.S. patent application Ser. Nos. 13/214,096, 12/820,968, 12/615,196, 61/375,699, 61/112,751, 61/168, 183, and 61/185,781 are hereby incorporated by reference.

BACKGROUND

A problem with rigid casts is that they are not adjustable in size. When a patient wears a cast, frequently the size of their limb will change due to atrophy or reduced swelling. When these changes occur, the cast cannot be adjusted to compensate for this reduced size. What is needed is an adjustable brace that can be adjusted so that individual regions of the brace or cast can be adjusted to the patient's body.

SUMMARY OF THE INVENTION

The present invention is directed towards a adjustable brace that can have a plurality of regions that inherently holds the inner surface of a non-planar structure in a three dimensional shape, which matches and/or corresponds to a digital representation of the surface of the limb, and which are independently adjustable and can extend along the length of the brace. These adjustable portions can be coupled to a non-adjustable portion that inherently holds its inner surface in a non-planar three dimensional shape that corresponds to a digital representation of a surface of the limb. Thus, the inner surfaces will retain a surface topography that corresponds to a digital representation of the surface of the limb when the brace is not being worn on the limb. In an embodiment, the adjustable brace can be printed with a material in the final three dimensional shape with inner surfaces have a topography that corresponds to a digital representation of the surface of the limb. The inventive brace is substantially different than a wrap-able splint which is made from a sheet(s) of flexible material.

These individual regions can be adjusted to proper size so that the patient's injured limb is properly supported. For example, an injured region can be swollen due to the injury. A custom cast or brace can be designed and fabricated for the swollen limb as described in U.S. patent application Ser. Nos. 12/820,968 and 12/615,196. A plurality of markings or points of visible or IR light can be projected to the patient's limb and the limb can be photographed by a plurality of infrared (IR) or visible light cameras. From the photographs, a three dimensional representation of the limb can be created by photogrammetry, image correlation, depth mapping or any other suitable IR and/or visible light photography based surface topography detection method. From the three dimensional representation, an adjustable non-planar brace can be designed having an inner surface that corresponds to the three dimensional representation of the patient's limb.

A doctor may mark the injured areas of the patient with a pen or any other suitable marker. Some of the markings can indicate the areas where the patient is injured such as bone breakage, or swollen areas, etc. Other markings can indicate an edge or a seam of the brace. These markings can be captured by the digital photographic images and the marking locations can be used to design the adjustable brace.

In an embodiment, the brace may include a first section that inherently supports one side of the patient's limb and a plurality of adjustable sections that support an opposite side of the limb. The adjustable sections can be attached to the first section by hinges and/or adjustable and releasable couplings. By releasing the releasable couplings, the adjustable section can be opened and the patient can insert or remove the limb from the brace. To secure the brace to the limb, the limb is placed in the first section of the brace and the adjustable sections are closed over the limb and the releasable couplings can be secured in the closed positions. The first section of the brace is non-planar and is formed in a three dimensional shape such that it inherently holds the inner surface in a pre-determined shape that corresponds to an outer surface of the limb that is supported by the brace. When the couplings of the brace are in the closed positions, the brace will provide not only support, but the brace structure also provides protection to the patent's limb, like a normal brace or cast both supports and protects the limb. As the limb cross section changes shape due to swelling, healing or atrophy, the adjustable sections can be moved to provide a proper fit to the patient until the healing is complete.

The adjustable brace can have various different configurations. In an embodiment, the first section can be coupled to the adjustable sections along one edge with a plurality of hinges and a plurality of adjustable fasteners on the opposite edge. As the surface of the patient changes, the corresponding adjustable section can be moved by rotating the adjustable section about the hinge. The adjustable fasteners can include a locking mechanism that allows the adjustable sections to be set at a specific cross section size and prevents the cross section from expanding or compressing. When the adjustable section is at the proper position, the adjustable fastener can be locked. The brace can be adjusted as many times as necessary to help the patient recover.

In another embodiment, the adjustable brace can also be adjusted at both the adjustable fastener side and the hinge side. By adjusting the brace at opposite sides, the cross section can be adjusted more uniformly and may provide a better fit for the patient. In this embodiment, adjusting mechanisms can be attached to an edge of the first portion of the brace that is adjacent to the hinge. A second locking mechanism can be used to secure the adjusting mechanisms in place. With the adjustable mechanisms on both sides locked in place, the brace cannot expand or compress in cross section. In other embodiments, various other combinations of hinges, adjustable mechanisms and locking mechanisms can be used in any embodiment of the three dimensional non-planar adjustable brace.

In other embodiments, the brace can include a plurality of sets of pads that can be removably coupled to the outer brace structure. The outer brace structure can have fenestrations for ventilation and to decrease the brace weight. The padding sets can include couplings that engage the fenestrations. In an embodiment, the padding can have a large number of smooth flexible surfaces that support the patient's limb and provide ventilation. A first padding set can be designed to have an interior surface that corresponds to the surface of the patient's injured limb. Additional sets of paddings can be designed with different interior surfaces which correspond to the injured limb after the swelling of the injury has gone down or after the limb has changed in cross section due to atrophy or other anticipated surface changes. In other embodiments, the patient's limb can be removed from the brace and photographed again to obtain current surface data that can be used to create a new padding set that can replace the prior padding. In these embodiments, a fixed or adjustable brace shell can be used with multiple sets of pads to provide a proper fit for the patient over a period of time and throughout changes to the patient's anatomy.

The inventive custom design process is unique because it provides a virtual fitting of the brace to the patient prior to fabrication of the actual device. No other known system provides the ability to design custom, adjustable, non-planar, three dimensional braces in a virtual manner. In particular, the inventive process can detect markings placed on a body and utilize this information to design the adjustable brace based upon the location of the marks.

In yet another embodiment, a brace or cast can be designed having a plurality of accessible regions. Each region can be attached to a hinge or other releasable fastener that allows the portion of the brace for access to the patient. This can be designed over a specific area of interest, for example a wound area that needs to be cleaned or periodically checked and then protected again. By placing a number of these accessible regions adjacent to each other, the body can be cleaned by opening each region individually while the rest of the body is held within the device that inherently has internal surfaces that correspond to the surface of the injured limb. The inventive brace allows improved comfort and hygiene while still protecting the patient during the healing process. For instance, the inventive brace continuously holds and protects all regions that do not need to be accessed, while allowing access to regions that need to be accessed. This feature can be particularly useful for medical procedures that may require placing pins or other objects in a patient. It may be necessary to avoid contact with and allow inspection of these areas. By using an access region over these areas, the doctor will be able to inspect the area to insure that the patient is healing properly, while the other portions of the limb are still supported and protected by the brace. The accessible region feature can also be particularly useful for infants who will need to be cleaned regularly. The inventive brace can be designed with access to the lower torso regions that allow the child to be cleaned. The region can be opened for cleaning and then closed after cleaning is completed. This design is a significant improvement over casts that must be partially sawed to access the child for cleaning.

In an embodiment, the brace or cast has a smooth inner surface that conforms to the scanned surface of the limb. Because the inner surface of the brace accurately conforms to the patient, the brace can be worn by the patient without any padding. This is an improvement over splints and casts that must have a layer of soft breathable material in contact with the skin. The brace can be made of a hard plastic material and the inner surface of the brace should also be very smooth. In order to be comfortable, the inner surface can have a surface finish of less than 500 $R_a\mu$ inch. A brace or case that can be worn by a patient without padding has several benefits including: simplified brace design and construction, less weight, lower profile, better ventilation, no absorption of water, easier cleaning, etc.

While the device has been described as an adjustable brace or cast for humans, in other embodiments, it is possible to use the invention for other products used by humans including: adjustable custom chairs, seats, saddles, athletic equipment, shoes, padding, helmets, motorcycle and bicycle seats, handlebars and hand grips, etc. The described apparatus and method can also be used for braces and casts for animals and custom saddles for horses and equestrians.

DETAILED DESCRIPTION

The present invention is a custom designed, adjustable cast or brace having interior surfaces that correspond closely to a body. When a patient injures a limb, such as a broken bone, there can be a swollen area around the injury. The adjustable brace can be designed to closely fit around the limb when it is initially injured. As the injured limb heals, the swelling can go down, which results in an open volume between the limb and the cast or brace. This open volume reduces the support for the bone and the limb. When an open space is detected, the adjustable brace can be adjusted to reduce the cross section of the brace at the region that surrounds the portion or portions of the limb that are now smaller in size. Thus, the adjustable brace can be adjusted to accurately fit the patient's anatomy as the surface changes.

Figure 1:
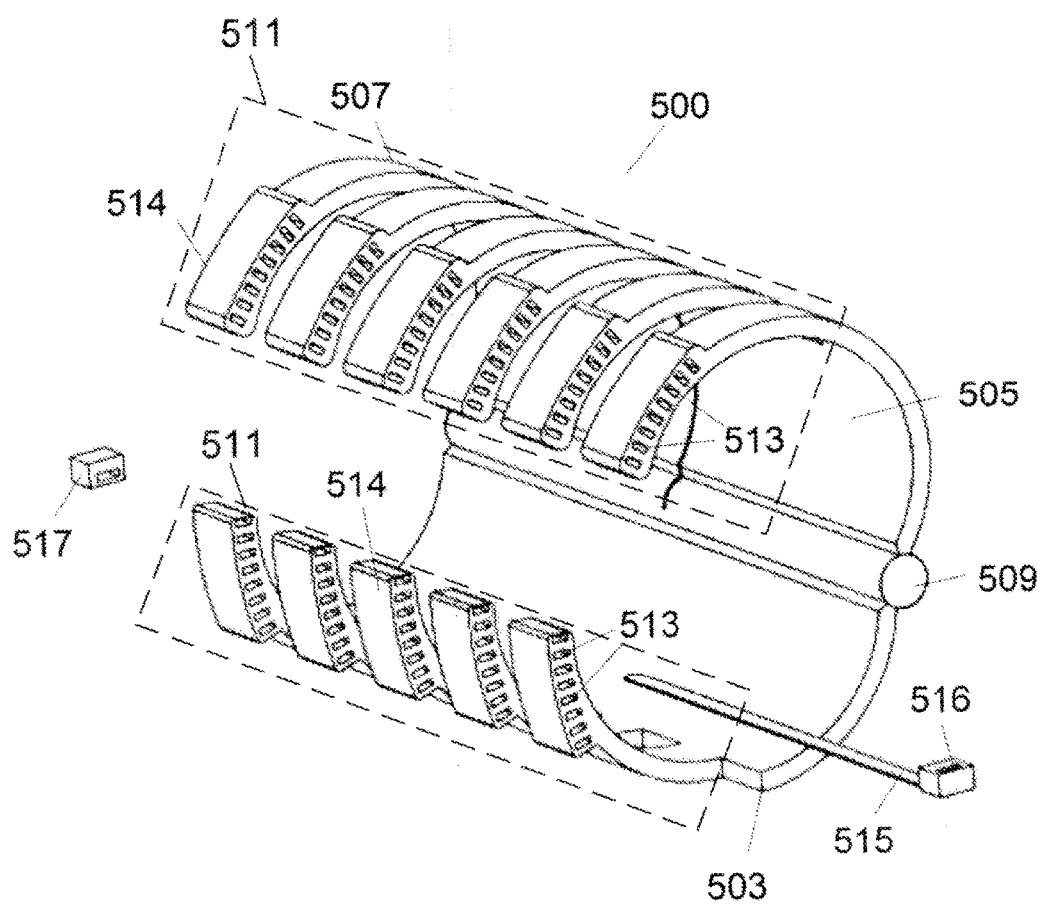
FIG. 1-3 illustrates an embodiment of an adjustable brace.

With reference to FIG. 1, an embodiment of an adjustable brace 500 is illustrated having a first lower portion 503 and a first upper adjustable portion 505 and a second upper adjustable portion 507. The lower rigid portion 503 is coupled to the first upper adjustable portion 505 and the second upper adjustable portion 507 by hinges 509 that allow the adjustable brace 500 to be opened to allow the user to insert or remove the limb. The hinges 509 also allow the adjustable brace 500 to be closed to support the limb. The adjustable brace 500 also includes a plurality of adjustable couplings 511 that allow the first upper adjustable portion 505 and the second upper adjustable portion 507 to be adjusted to the proper position around the patient's limb and secured in the desired position. In an embodiment, the adjustable couplings 511 can include a plurality of fingers 514 that have a plurality of adjacent slots 513. In an embodiment, the first portion is for supporting a first surface of a limb and an adjustable portion is coupled to the first portion to support a second surface of the limb that is opposite the first surface of the limb. The brace can be created in the final three dimensional form that it will be worn in and the first portion of the brace may inherently hold the first portion in a first position that may correspond to a digital representation of the first surface of the limb. Furthermore, in this embodiment, the second portion can inherently hold the inner surface of the adjustable portion in a second shape, which may correspond to a digital representation of the second surface of the limb. The portion(s) of the adjustable brace may be created in their final form from a plastic material using a 3D printer.

Figure 2:
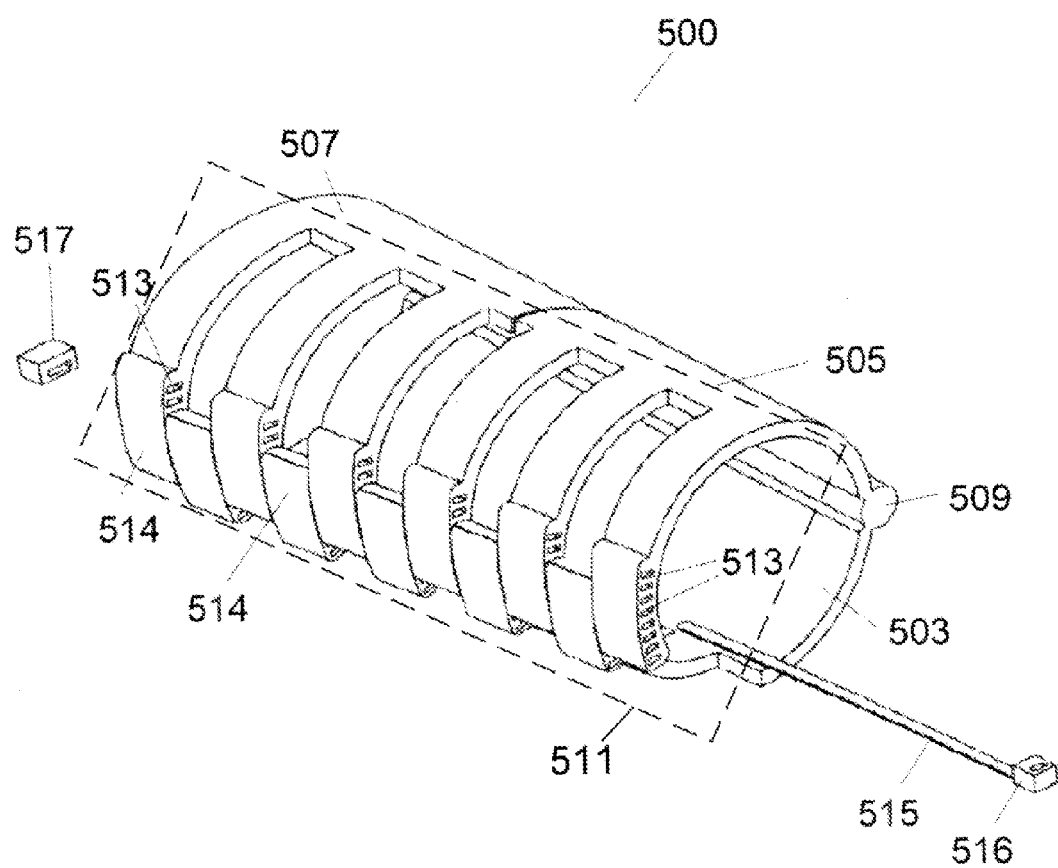

With reference to FIG. 2, the adjustable brace 500 is shown in the closed position with the cross sections of the adjustable brace 500 substantially uniform. The slots 513 of the adjustable couplings 511 can be aligned and an elongated structure 515 can be placed through the aligned slots 513. The fingers 514 of the adjustable portions 505, 507 can be offset from the fingers 514 of the lower portion 503 so that when the brace 500 is closed, the fingers 514 will overlap each other. By varying the amount of overlap of the fingers 514, the internal cross of the brace 500 can be adjusted to properly support and protect the patient's limb. In order to insure proper alignment, some or all of the slots 513 may be equidistant from the hinge 509. Thus, regardless of the relative positions of the brace portion 503, 505, 507, if there is overlap between the fingers 514, the slots 513 will be properly aligned. In an embodiment, the adjustable brace has a hinge coupled to a second edge of the first portion opposite the first edge for coupling the second edge of the first portion to the adjustable portion.

Figure 8:
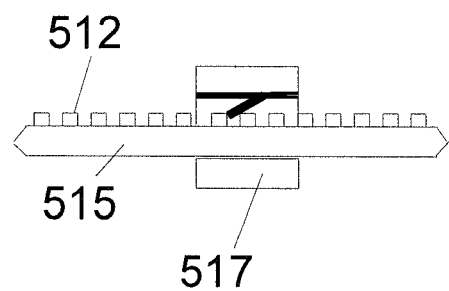

In an embodiment, an end 516 of the elongated structure 515 can be larger than the slots 513 so that the end 516 cannot pass through the slots 513. When the elongated structure 515 is fully inserted, a locking mechanism 517 can be secured to the end of the elongated structure 515 to keep the elongated structure 515 in place as shown in FIG. 8. Once the elongated structure 515 is placed through the aligned slots 513 and the locking mechanism 517 is placed on the end of the elongated structure 515, the adjustable couplings 511 can be locked into position. With the adjustable couplings 511 locked, the adjustable brace 500 can be a rigid structure protecting the patient's limb. In an embodiment, the adjustable portion of the adjustable brace is adjustable to alter the cross sections of the brace.

Figure 3:
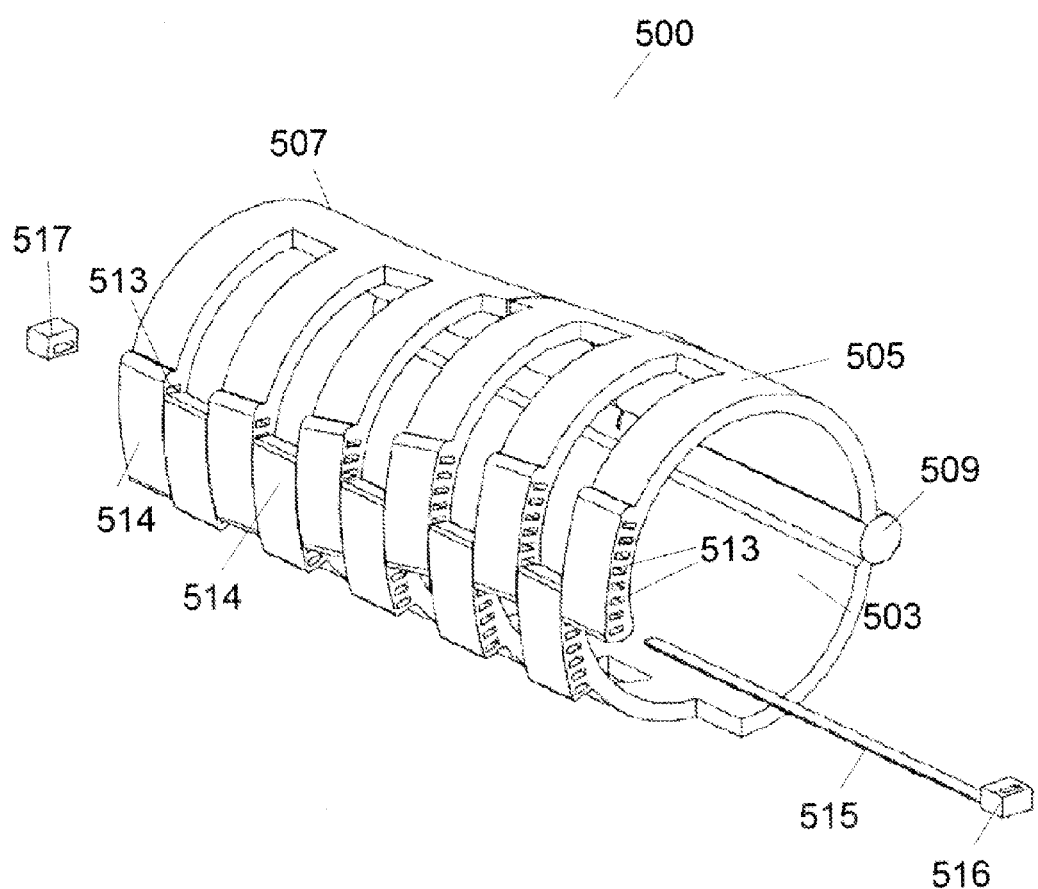

With reference to FIG. 3, the adjustable brace 500 can be adjusted to have a larger cross section at the first upper adjustable portion 505 than the second upper adjustable portion 507 by altering the overlap of the fingers 514. In this example, there is less overlap of the fingers 514 at the front end of the first and second adjustable portions 505, 507 than the back end. There is also more overlap of the fingers 514 of the second adjustable portion 507 than the first adjustable portion 505. The plurality of slots 513 are aligned and the elongated structure 515 can be placed through any of the slots 513 to hold the adjustable brace 500 in the desired position. In this embodiment, the first upper adjustable portion 505 and the second upper adjustable portion 507 can bend or twist to accommodate the change in cross section.

Figure 4:
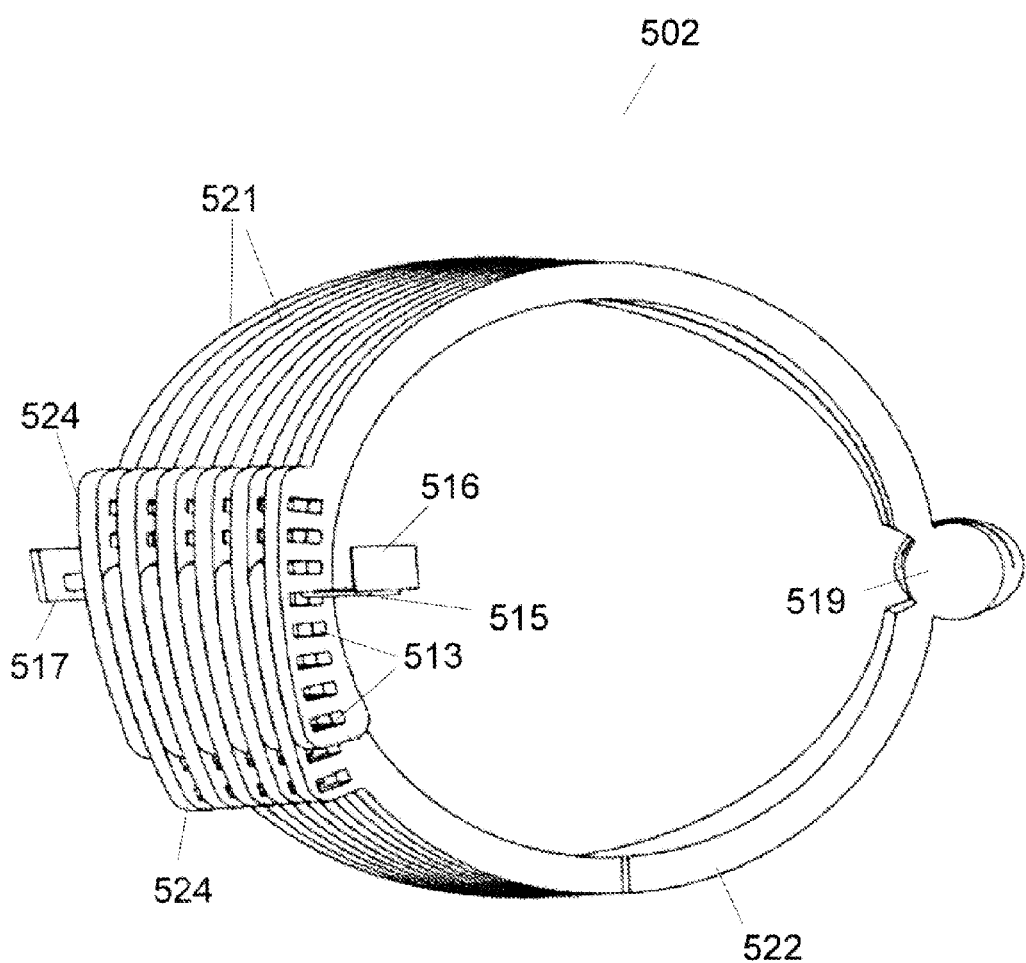
FIG. 4 illustrates an embodiment of an adjustable brace having thin adjustable portions.

With reference to FIG. 4, in other embodiments, an adjustable brace 502 can have many narrow width adjustable sections 521 that are each individually adjustable that are coupled to a lower section 522 by a plurality of hinges 519. By having more narrow width adjustable sections 521, the adjustable brace 520 can be more accurately adjusted to fit around the patient's injured limb. For example, there is a small swollen area of the patient; one or more of the thinner adjustable sections 521 can be adjusted to match the topography of the small swollen area. As the swelling decreases, these one or more adjustable sections 521 can be adjusted to reduce the brace cross section. The brace 502 can include offset fingers 524 that each have a plurality of adjacent slots 513. An elongated structure 515 can be placed through some of the aligned slots 513 and a locking mechanism 517 can be used to keep the elongated structure 515 in place.

In other embodiments, different width adjustable sections can be combined. For example, an adjustable brace may have thinner adjustable sections over the injured portion of the limb and wider adjustable sections at the ends of the brace. By placing thinner adjustable sections over the injury, the brace can be more accurately adjusted to properly support and protect the limb as the injured area heals.

Although the adjustable braces illustrated in FIGS. 1-4 can be adjusted to roughly match the patient's changing topography, the change in cross section is not uniform. Because the rigid and adjustable portions are connected by hinges, if the cross sections are changed significantly, the cross section of the brace can go from a circular shape to an oval shape with a slight angle at the hinge. In order to more accurately adjust the brace, adjustable connectors may be attached to opposite sides of the adjustable brace.

Figure 5:
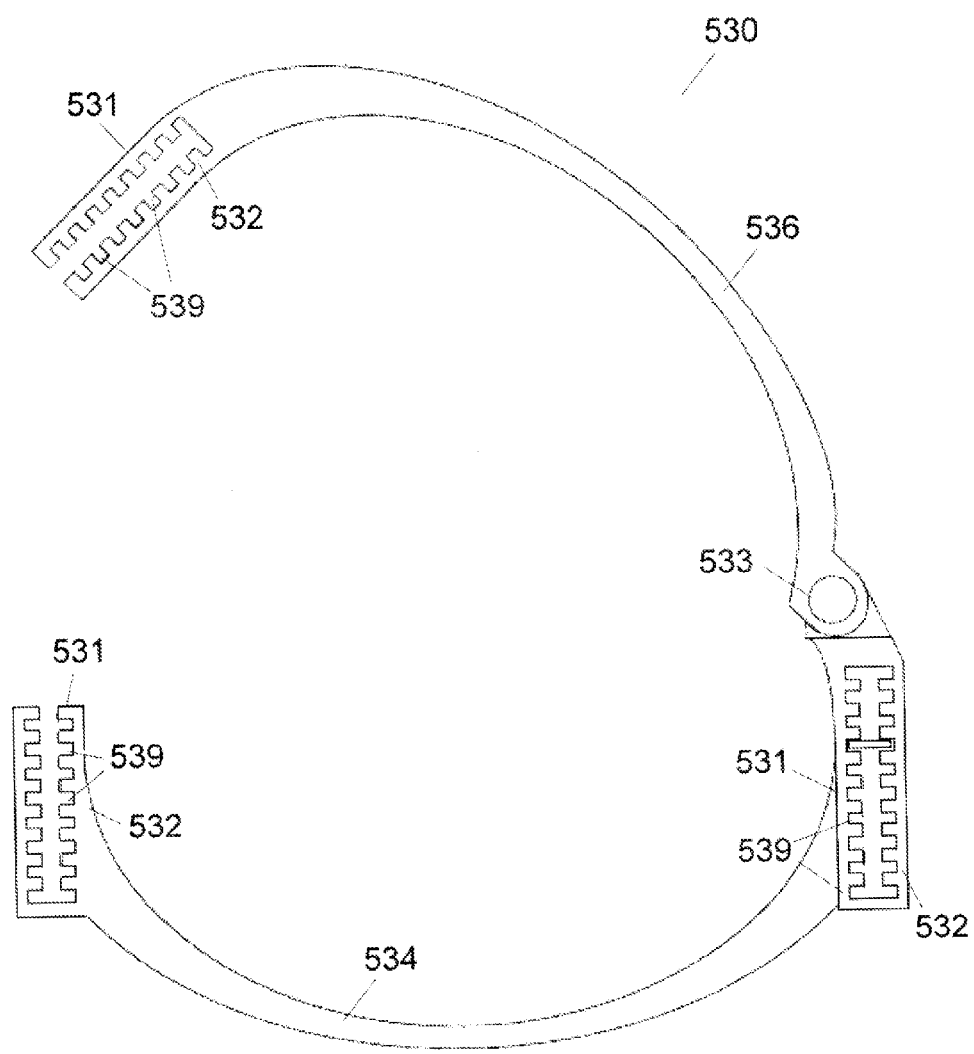
FIGS. 5-6 illustrate an embodiment of the adjustable brace having adjustable couplings on opposite sides of the brace.
Figure 6:
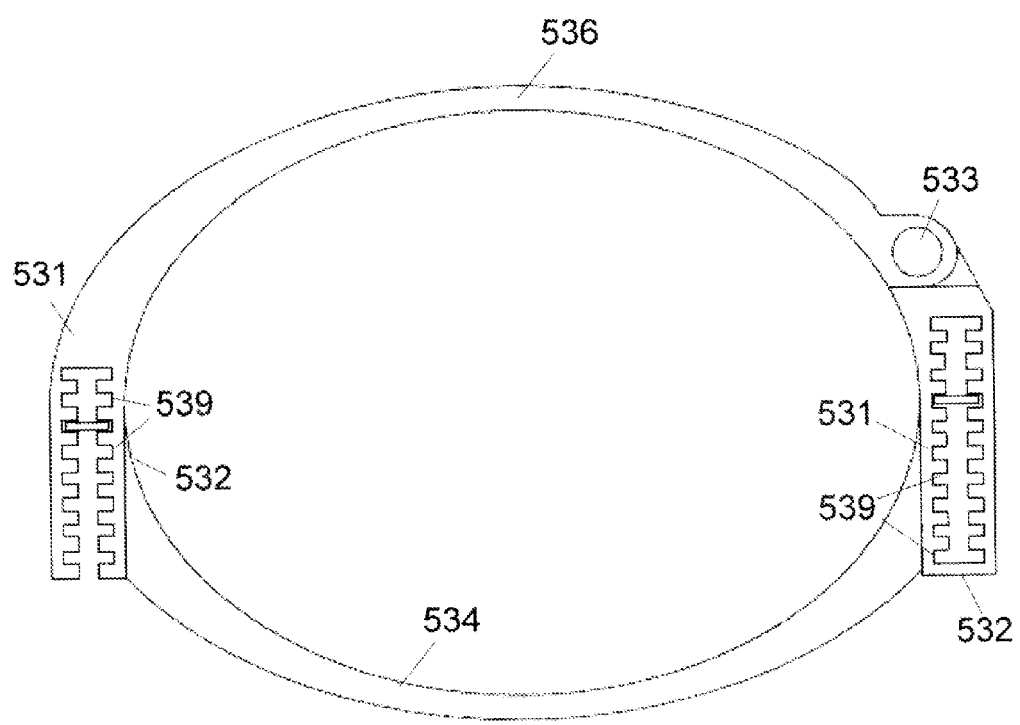

With reference to FIGS. 5 and 6, an embodiment of an adjustable three dimensional non-planar brace 530 is illustrated having a lower portion 534 and an upper portions 536 that are attached to each other with adjustable couplings 531 on opposite sides. FIG. 5 shows the brace 530 in the open position and FIG. 6 illustrates this embodiment of the brace 530 in the closed position. The adjustable couplings 531 on either side of the brace 530 allows the brace 530 to be more accurately adjusted to the changing topography of the patient's injuries. In an embodiment, the adjustable couplings 531 can be similar to the adjustable couplings illustrated and described with reference to FIGS. 1-4. The adjustable couplings 531 may include a plurality of slots 539 formed in offset fingers 532. The cross sections of the brace 530 can be adjusted by the overlap of the fingers 532. The cross section is reduced when there is more overlap of the fingers 532 and increased when there is less overlap. The brace 530 can be adjusted equally on both sides if the change in cross section of the patient's limb is uniform, or unequally if the change in topography is greater on one side. In addition to the adjustable couplings 531, the brace 530 can have a hinge 533 which allows the brace 530 to open as shown in FIG. 6. The brace 530 may be locked into a set position by inserting an elongated structure 515 through some of the aligned slots 539.

Figure 7:
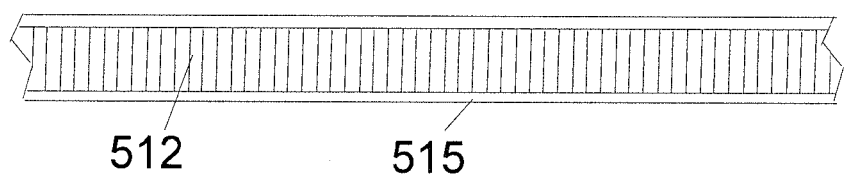
FIGS. 7-8 illustrate an embodiment of an adjustable coupling locking mechanism.

With reference to FIG. 7, in an embodiment, the elongated structure 515 can be a "zip tie" that fits within the slots 513 of the fingers 514 of the adjustable couplings shown in FIGS. 1-4. One side of the elongated structure 515 can include a plurality of grooves 512 that extend across the width of one side of the elongated structure 515. In other embodiments, any other locking mechanism that keeps the elongated structure 515 in the slots 513 can be used.

Although the zip tie is a common consumer product, a custom production run may create a specifically regulated color or logo which would not be available to the consumer. If the original custom zip tie is removed, it would not be easily replaced by the patient and this missing component would offer evidence of tampering with the brace.

Figure 9:
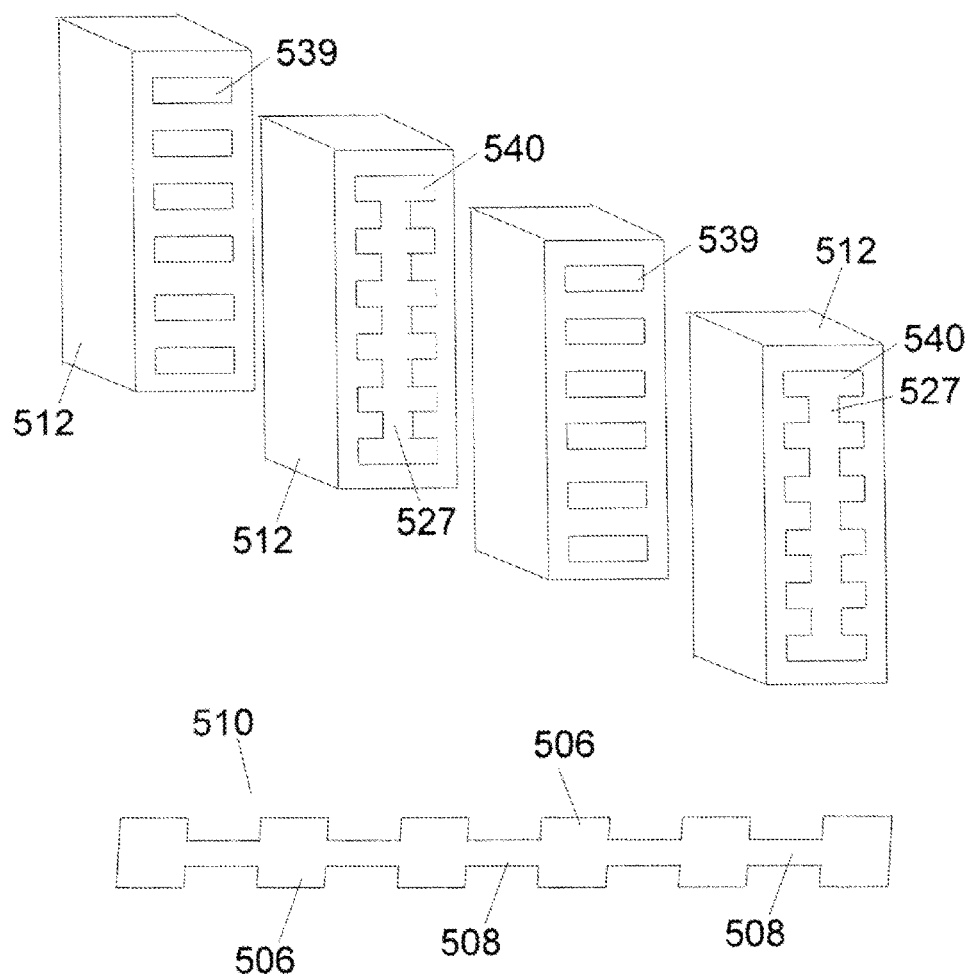
FIG. 9 illustrates an embodiment of an adjustable coupling locking mechanism.

With reference to FIG. 9, in an embodiment, the fingers 514 for one portion of the three dimensional non-planar brace may include connected slots 540 and other fingers 514 for an opposite portion of the brace may include normal slots 539. Rather than using an elongated structure having a uniform width, this embodiment, may use an elongated structure 510 having narrow sections 508. In the locked position, the narrow sections 508 are positioned through the normal slots 539 and the wider sections 506 are placed in the connected slots 540. If an adjustment needs to be made to the brace, the elongated structure 510 can be moved so that the narrow sections 508 are placed in the connected slots 540 and the wider sections 506 are placed in the normal slots 539. The narrow sections 508 may be smaller in width than the openings 527 connecting the connected slots 540. This adjustment process may be easier to accomplish than completely removing the elongated member from the brace if adjustments are necessary.

The cast or brace can have a smooth inner surface that corresponds closely to the patient's body and may also have an integrated construction. Such an inner surface provides the advantage of eliminating the need for a soft breathable material layer in contact with the skin. The cast or brace can be designed by an industrial designer using a Computer Aided Design (CAD) computer program. The mechanical data for a patient can be obtained from visible or infrared (IR) light photographs of the patient's body or limb. This body topography can be determined from the photographs and the topography data is then digitized and input into a CAD program that is referenced to design the cast or brace. An example of a suitable CAD program is Pro/Engineer by Parametric Technology Corporation. Other CAD software includes:

SolidWorks by SolidWorks Corporation a subsidiary of Dassault Systemes, S. A. For simplicity, the inventive custom brace, cast or device will be described as a back brace, however the same processes can be used to form an arm or leg brace or any other body brace, cast or device. The brace can be a hard and strong structure that is designed to surround and inherently hold the injured portion of the body or limb in a shape that corresponds to a digital representation of the surface of the limb.

For example, a leg brace is created for a patient using a CAD system. The leg brace can include an upper leg, knee, lower leg, and foot and have an interior surface that matches the mechanical dimensions and surface contours of the patient's leg. In order to accurately create an interior surface that matches the patient's leg, the surface counters of the user's leg are measured. The measurement of the outer surface of the leg can be obtained in several different ways. In a preferred embodiment, a photogrammetry, depth mapping or image correlation technique or other type of photographic surface detection method is used to obtain the outer surface measurements which can be a set of 3-dimensional coordinates that define the outer surface of the patient's leg or any other body part.

Photogrammetry in its broadest sense reverses the photographic process by converting flat 2-dimensional images of objects back into the real 3-dimensional object surface. Two or more different photographs can be required to reconstruct a 3-dimensional object. In a perfect photogrammetry process, two photographs would provide enough information to perfectly reconstruct the 3-dimensional object. Unfortunately, the photography and measuring process are generally not perfect, so the reconstruction of the 3-dimensional object based upon two photos will also have defects. The photogrammetry object measurement process can be improved by taking more photographs and using the extra information to improve the accuracy. The photogrammetry process will produce a set of 3-dimensional coordinates representing a surface of an object from the measurements obtained from the multiple photographs.

Photogrammetry uses the principle of triangulation, whereby intersecting lines in space are used to compute the location of a point in all three, XYZ dimensions. In an embodiment, multiple cameras are used to photograph the leg or body part simultaneously. In other embodiments, a light from a light source that is a known distance from a camera is projected onto a patient and a photograph of the patient is taken. By triangulating each of the points of light, the distances from the camera to each point of light can be determined. In order to triangulate a set of points one must also know the camera positions and aiming angles also called the "orientation" for all the pictures in the set. A process called resection does the camera position and aiming angle calculations for each camera. The cameras should also be calibrated so their errors can be defined and removed.

Triangulation is the principle used by photogrammetry to produce 3-dimensional point measurements. By mathematically intersecting converging lines in space, the precise locations of the points can be determined. Photogrammetry can simultaneously measure multiple points with virtually no limit on the number of simultaneously triangulated points. By taking pictures from at least two or more different locations and measuring the same target in each picture, a "line of sight" is developed from each camera location to the target. Since the camera locations and aiming directions are known, the lines can be mathematically intersected to produce the XYZ coordinates of each targeted point. When a pattern of IR or visible light points are projected onto the patient, triangulation can also be used to determine the locations of these points based upon the distance between the light source and the camera and the detected angles of the points.

Resection is the procedure used to determine the coordinates of the object from photograph data, based upon the camera positions and aiming directions, also known as the orientation of the camera. Typically, all the points that are seen and known in XYZ coordinates in the image are used to determine this orientation. For an accurate resection, you may have twelve or more well-distributed points in each photograph. If the XYZ coordinates of the points on the object are known, the camera's orientation can be computed. It is important to realize that both the position and aiming direction of the camera are needed for resection. It is not sufficient to know only the camera's position since the camera could be located in the same place but be aimed in any direction. Consequently, the camera's position which is defined by three coordinates, and where it is aimed which is defined by three angular coordinates must be known. Thus, although three values are needed to define the X, Y and Z coordinates of a target point, six values may be required to define a point on a picture, XYZ coordinates for position, and XYZ angles for the aiming direction.

The surface being photographed should also have a minimum number of well-distributed reference points that appear on each photograph and for an accurate surface measurement. The reference points can be visible marks placed on the object that provide a visible contrast that will be clearly shown on the photographs. There should be at least twelve well-distributed reference points on each photograph and at least twenty points for the entire surface of the object. The reference points should be evenly distributed on the object and throughout the photograph. The surface of the object can be more accurately measured with a larger the number of reference points.

In an embodiment, the patient's natural features including: freckles, spots, wrinkles, pores and other features can be used as the reference points. Alternatively, IR or visible light can be projected onto the patient to provide the reference points for photographic measurement. It is also possible to mark the patient's skin with ink markers and in an embodiment, the patient or patient's limb can be covered with a form fitting material such as an elastic cotton tube, stockinette, leotard, body suit. With reference to FIG. 1, a patient 101 is illustrated wearing a body suit 103 that covers the patient's body, arms and legs.

In an embodiment, a computer program processes the photographic measurements to produce the final XYZ coordinates of all the measured points. In order to do this, the program triangulates the target points and resects the pictures. The program may also calibrate the camera. Typical accuracies of the three dimensional measurements can be very high under ideal operating conditions. For example, the measurements can be accurate to 50-100 microns (0.002" to 0.004"). However, the accuracy of a photogrammetric measurement can vary significantly since accuracy depends on several inter-related factors. Important accuracy factors include: the resolution and quality of the camera, the size of the object being measured, the number of photographs taken, and the geometric layout of the pictures relative to the object and to each other.

Photogrammetric measurements can be dimensionless. To scale a photogrammetric measurement, at least one known distance is required. The known distance can be a distance marked on the object, a known distance between cameras or a known distance between a light source and a camera. For example, if the actual coordinates for some targeted points are known, the distances between these points can be determined and the points can be used to scale the measurement. Another possibility is to use a fixture with targets on it and measure the fixture along with the object. Because the distance between the targets on the fixture is known, it can be used to scale the other measurements between reference points on the object. Such fixtures are commonly called scale bars. The patient topography dimensions can also be determined by knowing a distance between two cameras and the angles of lines between the cameras and the points on the patient. From this information, the distances between the cameras and the points on the patient can be determined by triangulation. Similarly, the patient topography dimensions can also be determined by knowing a distance between a light beam source and a camera, an angle of the light beams from a source and the angles of the light points detected by the camera. From this information, the distances between the camera and the light points on the patient can be determined by triangulation. The light can be infrared and the camera can be an infrared camera that produces infrared photographs.

In an embodiment, the inventive method is used to make a cast or a brace for an injured limb. A series of photos are taken of the injured limb. If the bone is broken, fracture should be reduced before the photos are taken. The photogrammetric processing methods described above are then used to obtain the surface coordinates of the injured limb. In order to define common surface points on the limb, reference points can be placed on the limb. The reference points can simply be any contrasting color points, patterns, shapes, objects, symbols or other optical indicators which are easily visible. The reference points can be black or colored ink marks that are placed on the body with a pen. In other embodiments, the reference points can be lights such as visible light infrared light, points or grids, stickers or objects or any other visible point of reference. In the preferred embodiment, the reference points are placed and evenly distributed around the entire limb or portion of the body that the brace is being constructed for.

Figure 10:
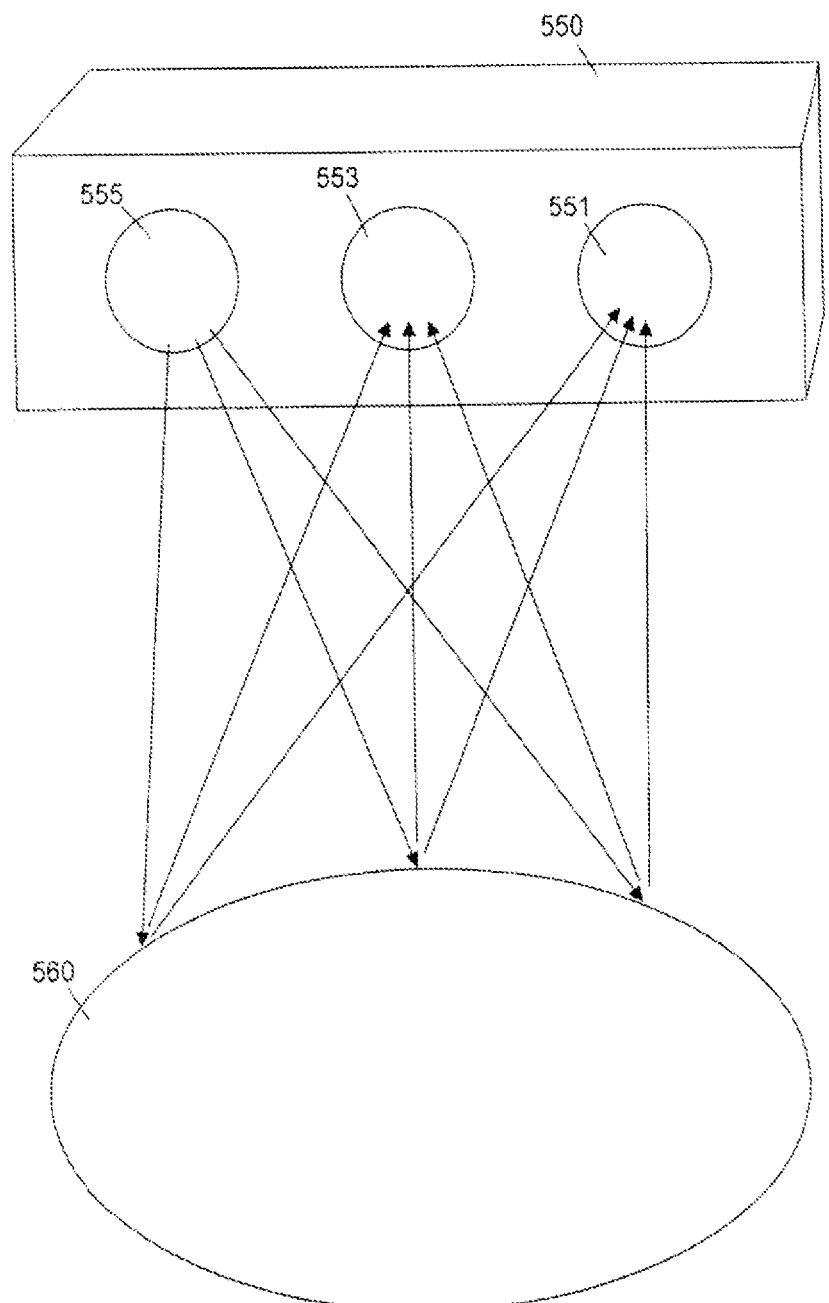
FIGS. 10-13 illustrates an IR and visible light photographic system(s) for detecting a surface of a patient.
Figure 11:
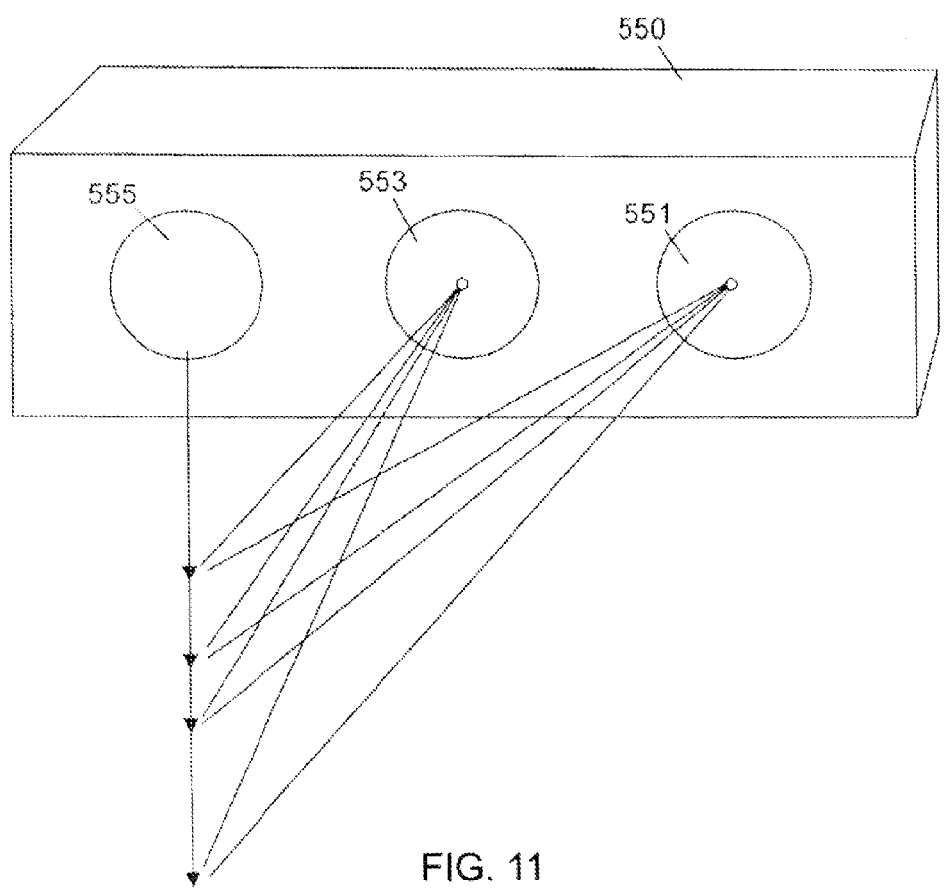

With reference to FIG. 10, in an embodiment the three dimensional surface data of a patient can be obtained using an optical device comprising a color image camera 551, an infrared (IR) camera 553 and an infrared (IR) light source 555 coupled to a signal processor. The IR light source 555, IR camera 553 and color image camera 551 can all be mounted on one side of the optical device 550 so that the color camera 551 and IR camera 553 have substantially the same field of view and the IR light source 551 projects light within this same field of view. The IR light source 555, IR camera 553 and color image camera 551 can be mounted at fixed and known distances from each other on the optical device 550. The color image camera 551 can provide color information for the patient's limb 560 or portion of the patient within the viewing region of the camera 551. The IR camera 553 and IR light source 555 can provide distance information for each area of the patient's limb 560 exposed to the IR light source 555 that is within the viewing region of the IR camera 553. The infrared light source 555 can include an infrared laser diode and a diffuser. The laser diode can direct an infrared light beam at the diffuser causing a pseudo random speckle or structured light pattern to be projected onto the patient's limb 560. The diffuser can be a diffraction grating which can be a computer-generated hologram (CGH) with a specific periodic structure. The IR camera 553 sensor can be a CMOS detector with a band-pass filter centered at the IR laser wavelength. In an embodiment, the color image camera 551 can also detect the IR light projected onto the patient's limb 560.

Figure 12:
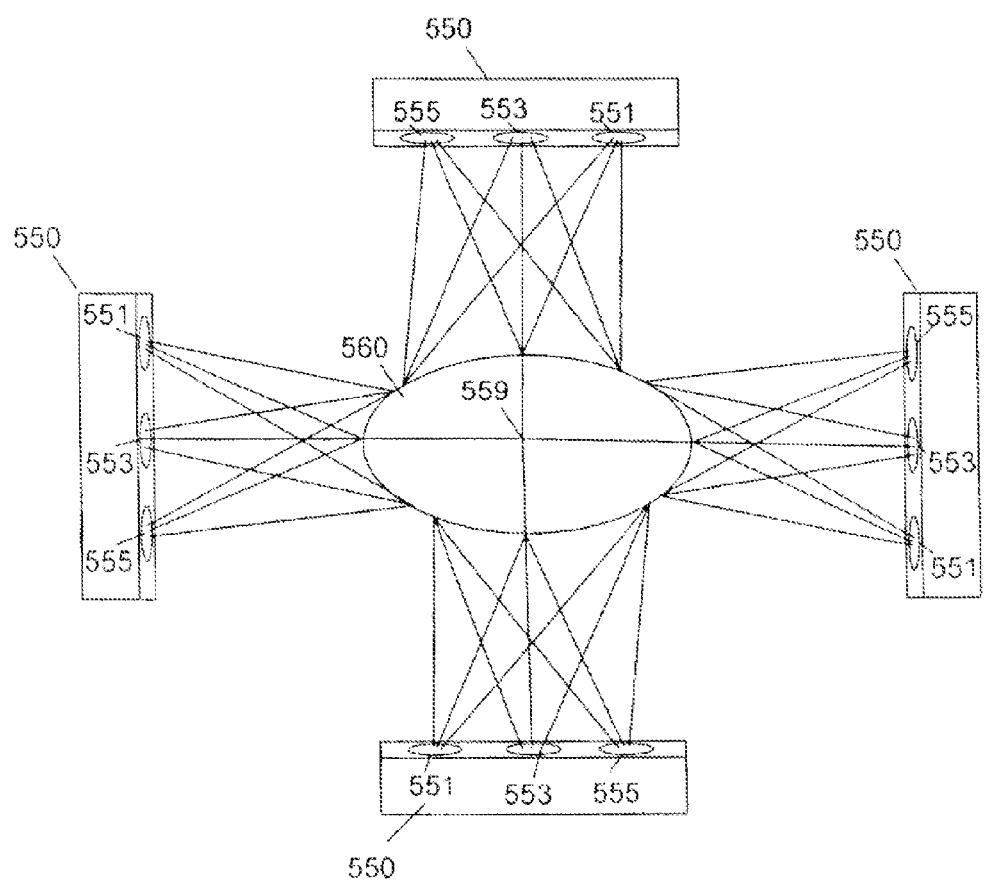

With reference to FIG. 12, the optical device 550 can detect the distance between the infrared camera 553 and the IR light on the patient based upon triangulation where the camera 553 sees the patient's limb at a different angle than the infrared light source 555, and the distance between infrared light source 555 and IR camera 553 is defined. The principle of structured light distance sensing is that given a specific angle between IR light source 555 and IR sensor 553 for each point of light on the patient's limb, and a distance between the object and the IR light source 555 or IR camera 553 or color camera 551 can be determined by triangulation. The angles of the light points on the patient's limb detected by the IR camera 553 and the color camera 551 will change depending upon the distance of the patient from the optical device 550. In an embodiment, a calibration process can be used to determine the angles of each light point on a plane at different distances from the optical device 550. By knowing the angles and corresponding distances for each point of IR light, the distance of the points of light from the optical device 550 can be determined. These distance calculations for an object can also be known as three dimensional mapping. The distance value for each light point can also be matched with the visible color image data so that color and distance information for each pixel of a patient image can be determined and stored.

Because a single picture can capture the patient in a fixed position, the IR light source 555 can be project the IR light on the patent and the IR camera 553 can take a single photograph of the patient 560. The color camera 551 may also simultaneously take a single photograph of the patient's limb 560. In other embodiments, multiple IR or color photographic images can be taken of the patient's limb 560 is in different positions, and the corresponding image shifts are directly related to distance from the camera. Each successive photographic image serves as a reference photograph for the next frame calculation so that the movement of the patient can be detected and the changes in the three dimensional mapping can be recorded.

As discussed, the IR camera can detect the light pattern projected onto the patient's limb and through triangulation, the distance between the IR camera and color camera and each point of the light pattern on the patient can be determined. However, the distance information for the points can only determine a three dimensional surface of the patient's limb or a portion of the patient's limb that is detected by the IR camera 553 or the color camera 551. With reference to FIG. 45, in order to determine a three dimensional surface around a patient's limb, multiple optical devices 550 can be placed around the patient, and the three dimensional surface information from each of these cameras can be combined to determine the three dimensional surfaces around a circumference of a patient's limb. In an embodiment, the IR light from each of the IR light sources 555 can be emitted simultaneously and the photographs from all of the IR cameras 553 and color cameras 551 can be taken simultaneously. In other embodiments, the IR light sources 555 can interfere with the IR cameras 553 that are not part of the same optical system 550. Rather than protecting IR light from all of the IR light sources 555 at the same time, the optical systems 550 can be configured to sequentially illuminate with IR light and photograph the patient's limb 560. A first optical system 550 will emit the IR light and take IR and color photos of the patient's limb 560. The first optical system 550 can then stop projecting IR light onto the patient's limb 560 and the second optical system 550 can then emit the IR light, take IR and color photos of the patient's limb 560. The second optical system 550 can then stop projecting IR light onto the patient's limb 560. This described process can be sequentially repeated for the remaining optical systems 550.

After taking the IR photographs, surface data for different sides of the patient's limb 560 can be combined from the optical systems 550 in various different ways. For example, the multiple IR cameras 553 can produce distance information for the photographed patient's limb 560 that can be combined using a photogrammetry process to determine a full or partial circumferential three dimensional representation of the patient's limb 560. The surface data from the optical systems 550 will include some of the same surface areas of the patient's limb 560 that were also captured by at least two of the adjacent optical system 550. Because the three dimensional shape data is the same, the system can identify these matching surface shapes and combine the surface data to obtain continuous surface data for the photographed portion of the patient's limb 560. In an embodiment, the optical systems 550 can be aligned around the patient 560 with the IR cameras 553 radially aligned in a planar manner and directed towards a center point 559 within a cross section of the patient's limb 560. The optical systems 550 can each produce surface data for a portion of the patient's limb 560. Because the IR photos are taken on a common plane, the surface data from the different optical systems 550 can be joined by determining the distance of the surface data from the center point 559. In an embodiment, a first set of calibration IR and/or color photographs can be taken by the optical systems 550 of a physical center point marker 559 without the patient's limb 560. IR and/or color photos can then be taken of the patient 560. From this information, the position of the center point 559 relative to the surface data of the patient 560 can be determined. By knowing the distances and alignment of the surface data to a common center point 559, the surface data from the different optical systems 550 can be combined. In an embodiment, the optical systems 550 can be arranged on direct opposite sides of the patient's limb 560. Although four optical systems 550 are shown, in other embodiments, two or more optical systems 550 can be used to obtain the surface data for the patient's limb 560. Three optical systems 550 may be required to have some overlapping surface data for the patient's limb 560.

Figure 13:
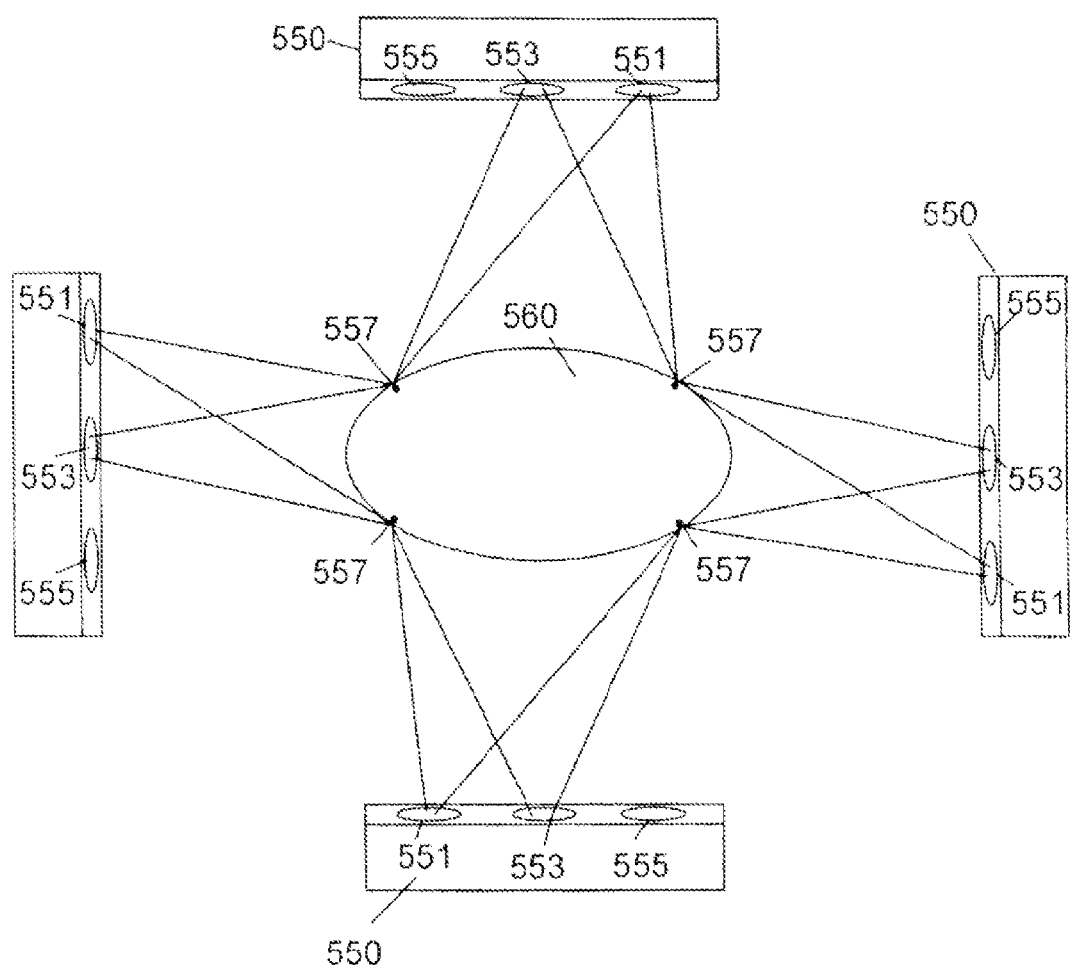

With reference to FIG. 13, in other embodiments the surface data from the optical systems 550 can be combined by using alignment markings 557 on the patient's limb 560. The patient's limb 560 may be covered with a material and a visible or IR marking 557 can be projected onto the patient's limb 560 at locations that are within the field of view of two or more optical systems 550. The color camera 551 may detect both visible and IR markings and the IR camera 553 may only detect IR markings. The optical systems can be able to distinguish the IR light from the IR markings because the shape of the IR marking 557 can be larger or may have a different shape. The surface data from adjacent optical systems 550 can be combined by using a photogrammetry or image correlation process that matches the positions of the markings 557 that are photographed by both optical systems 550.

Figure 14:
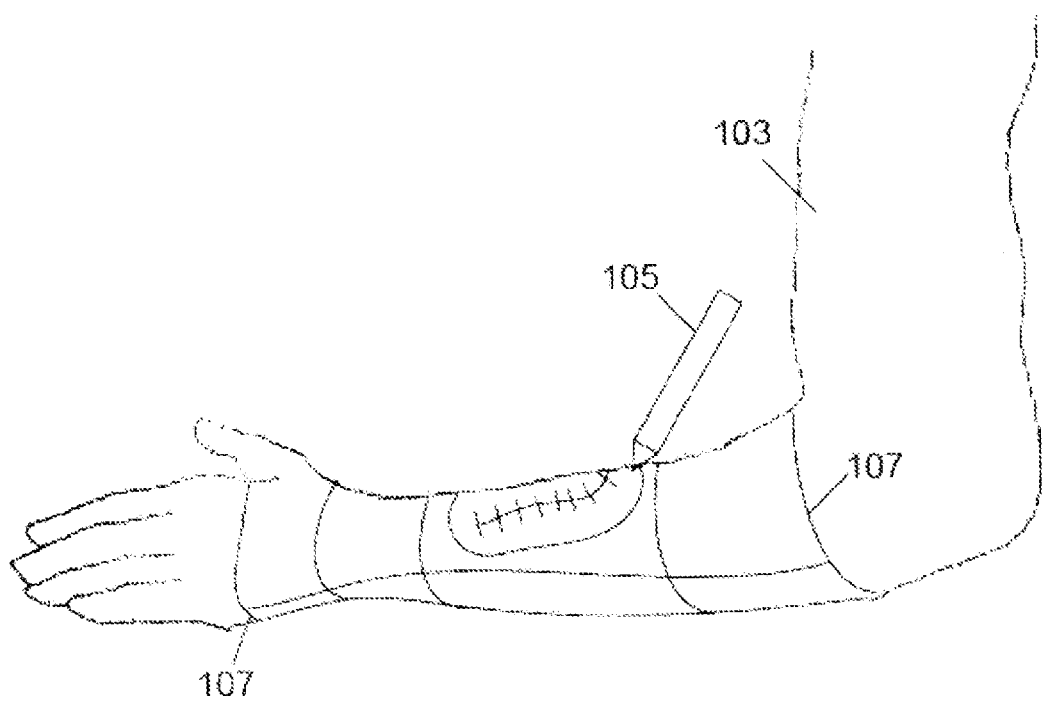
FIG. 14 illustrates a marked patient for detection by the photographic detection system.

In addition to the reference points, the patient can also be marked to define an edge of the brace, a seam of a modular brace or other features. With reference to FIG. 14, the doctor can mark the patient's arm 103 with a pen 105 to define the locations of the edge of the brace or a seam of a modular brace. The edge or seam marking can be one or more continuous ink lines 107 that extend around the patient's arm 103. In other embodiments, the edge or seam can be defined by a series of ink marks that define the edge of the brace and are connected during the brace design. Additional ink lines 109 can also be marked on the patient to create edges for the brace pieces. For example, the patient may have injured areas from an operation that has been closed with stitches and should not be in contact with the rigid brace. By providing an opening in the brace, the patient's stitches will not be pressed against the brace structure. In FIG. 1, the doctor has drawn a circle around this portion of the patient's body so that the brace can be designed with a cut out for this area. The doctor can also make notes on the patient's arm 103. For example, the doctor can write information indicating the location of the injury as well as information indicating the locations of bones, joints, tendons and ligaments. These anatomical locations are important in the design of the brace and are therefore marked on the patient's arm 103. Because photogrammetry uses photographs, the digital pictures will record all of the ink lines or other ink markings.

Figure 15:
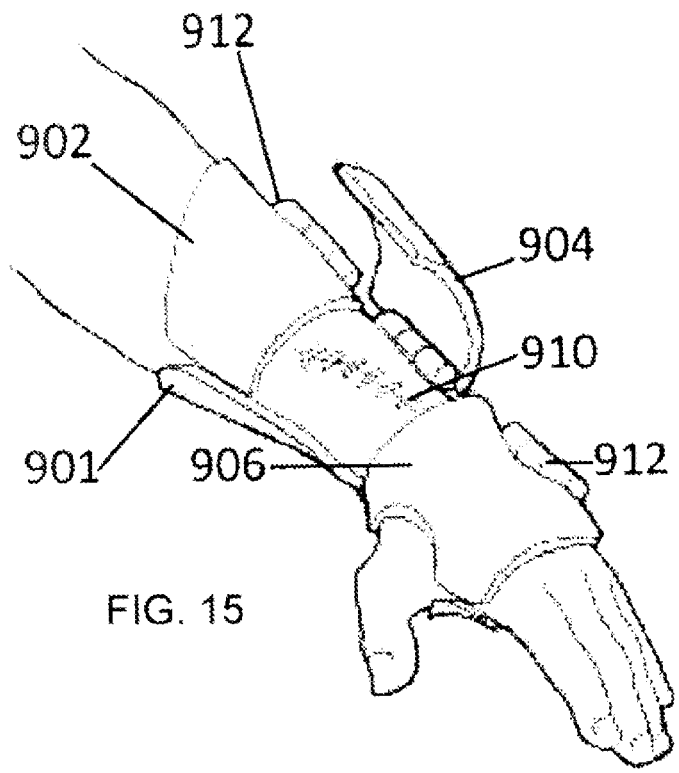
FIGS. 15-16 illustrate a brace having accessible regions.
Figure 16:
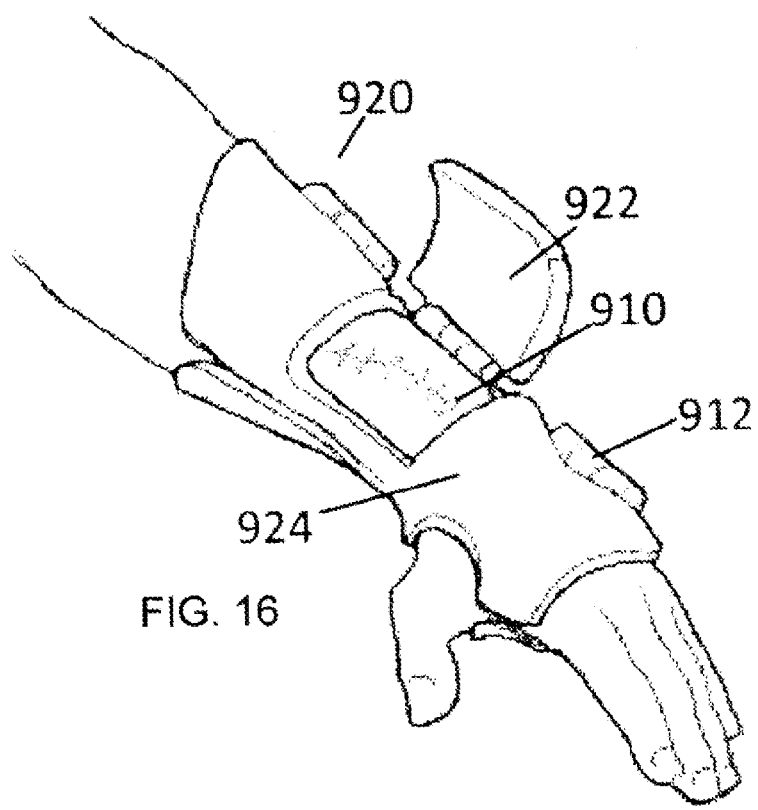

With reference to FIG. 15, in an embodiment, the brace 901 can have a plurality of accessible regions 902, 904, 906. The access regions 902, 904, 906 can be large or small depending upon the injury and patient. The different regions 902, 904, 906 may be marked on the patient prior to photographing. Each access region 902, 904, 906 can be attached to a hinge 912 or other releasable fastener that allows the individual portions of the patient covered by the brace 901 to be accessed. The access regions 902, 904, 906 can be strategically placed over a specific area of interest, for example a wound area that needs to be cleaned or periodically checked. In this way, the non-adjusting regions remain in place, inherently holding the body region in a shape that corresponds to a digital representation of the limb. In other embodiments, the access regions 902, 904, 906 can also extend along the entire length of the brace 901. The entire limb or body area covered by the brace 901 can be accessed for cleaning, inspection, removal of stitches 951 or other reasons by opening each region 902, 904, 906 individually while the rest of the limb or body is protected and immobilized by the brace 901. With reference to FIG. 16, in another embodiment, the brace 920 can have an individual access region 922 and the rest of the upper portion 924 of the brace can be coupled together. Releasable and adjustable couplings can be attached to the access regions 902, 904, 906 to secure the brace 901 in the closed position when the access regions 902, 904, 906 are closed.

With reference to FIGS. 17-22, in an embodiment, the brace 930 can be a modular design that can have a modular construction with modular sections that can be completely removed from the brace 911. This design can be useful for a broken limb bones such as a forearm. Casts are well known in the medical art. When a bone is broken, the bones can be set to reduce the size of the fracture and a cast is placed around the hand, lower arm and upper arm. As the arm heals, the casts are removed and replaced with smaller casts. A patient can go through several cast replacements depending upon the type of break. This can be very time consuming because each cast must be sawed off and a new shorter cast must be constructed over the arm or leg. Also as discussed, the application and removal of casts with a cast saw can be very traumatic to children who may need to be sedated during these procedures.

In an embodiment, a modular brace 930 can be designed for a patient that can have several modular adjustable brace sections including: an upper arm 940, cuff 942, elbow 938, lower forearm 932, upper forearm 934 and thumb spica 936. The sections can be coupled together with any of the described releasable fasteners or any other suitable fasteners. The sections can be removed from the modular brace 930 sequentially as the patient heals. As discussed above with regard to FIG. 14, the patient can be marked at the junctions between the different module and adjustable sections. The markings are detected by the photographic surface detection process and the different module sections are designed into the brace 930. Because x-rays are normally taken of broken bones, this x-ray data can be viewed with the photographic images and the brace 930 can be designed with the required structural integrity to protect the arm at the damaged areas of the body. The brace 930 is designed as described and the adjustable and modular sections can be secured to each adjacent section by removable fastener that have been described or any other type of couplings that are formed in the brace or attached to the modular sections such as screws 915.

Figure 17:
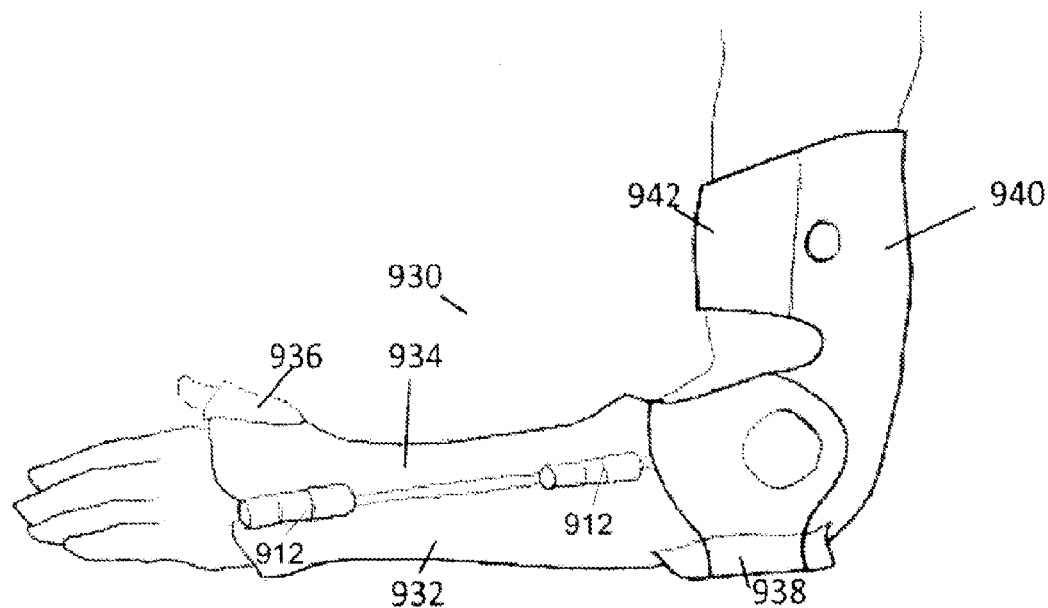
FIGS. 17-22 illustrate a modular brace.
Figure 18:
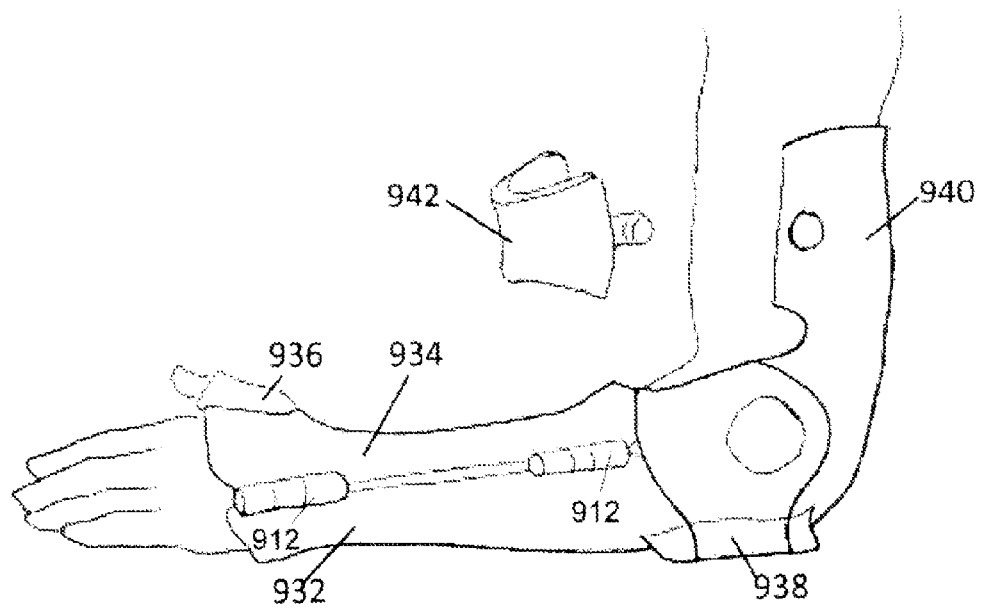
Figure 19:
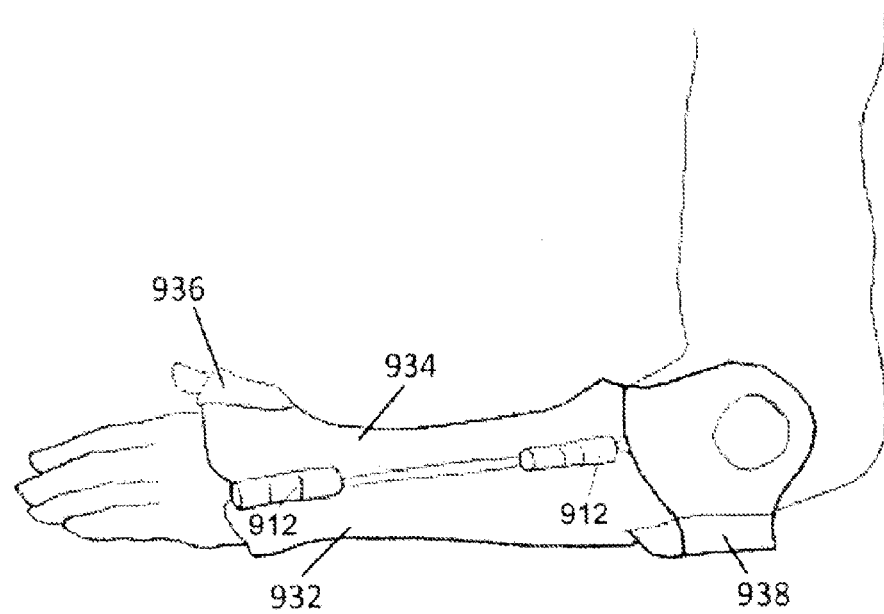

With reference to FIG. 17, if a patient breaks an arm, the entire arm may initially be immobilized with a brace 930 that extends from the fingers to the shoulder. With reference to FIG. 18, after a first period the cuff 942 can be removed from the upper arm module 940. This allows the elbow to flex after a period of isolation. If the cuff 942 is hinged to the upper arm module 940, the coupling can be opened. Alternatively, the cuff 942 can be coupled to the upper arm module 940 with any of the described adjustable releasable fasteners to remove the cuff 942. With reference to FIG. 19, after a second period, the entire upper arm module 940 can be removed when appropriate for treatment to allow the elbow flexion. An elbow module 938 still exists which surrounds the elbow and allows flexion, but does not allow for rotation.

Figure 20:
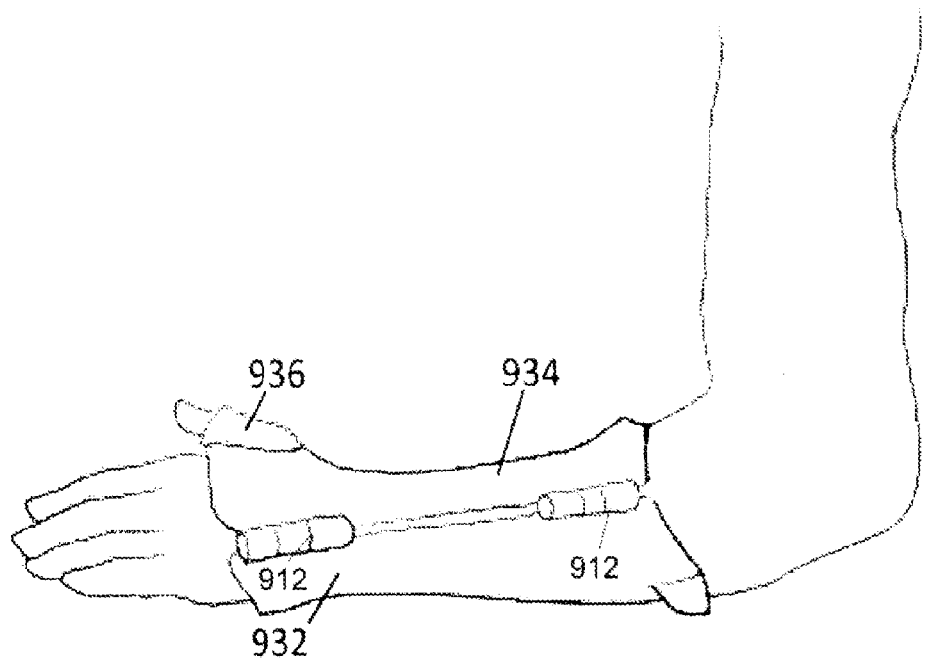
Figure 21:
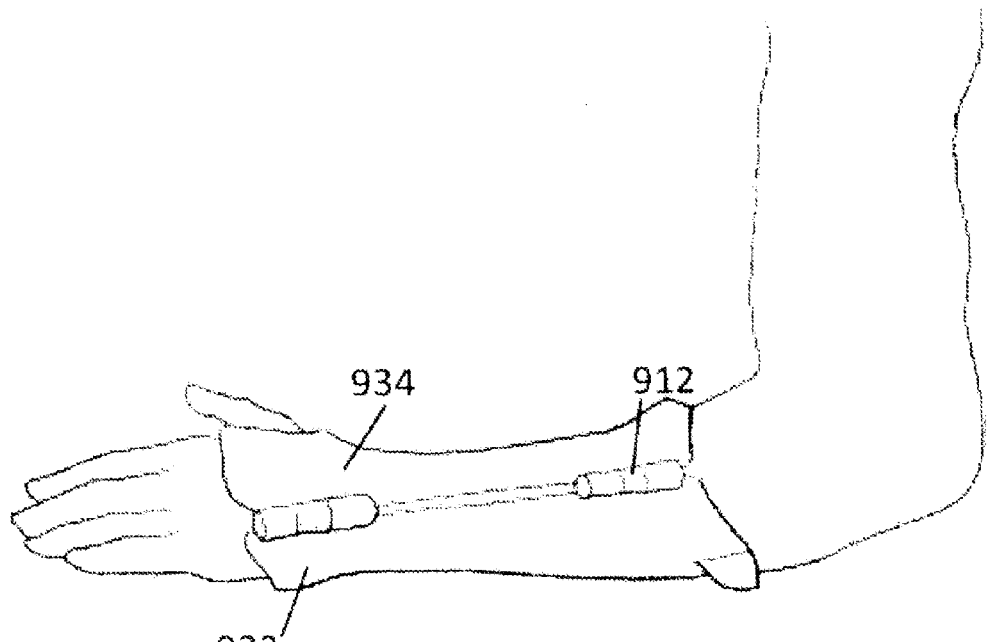

With reference to FIG. 20, the elbow module 938 is removed leaving a 'short arm' cast for the remainder of the treatment. This upper forearm 934 can be coupled to the lower forearm 932 with a hinge 912 and may be opened temporarily for cleaning of the skin and inspection, though it will be closed in order to keep the arm stabilized during the treatment. With reference to FIG. 21, the 'thumb spica' 936 may be removed at any time during the treatment, allowing motion for the thumb. Finally, with reference to FIG. 22, lower forearm module 932 of the brace 930 may remain as a 'splint' that may be held in place by a releasable strap such as a Velcro strap, if needed after treatment for additional stability and safety. This is in contrast to a flexible planar structure, which requires fasteners in order to maintain its conformation around the limb.

In other embodiments, a similar brace can be made for an injured hand, foot or leg. For example, when a patient injures a hand, the entire hand may initially need to be placed in a modular brace that includes different modules for the wrist, palm, fingers and thumb. The brace may also include access portions. The doctor can mark the area that is injured as well as the desired locations for each of the module seams and access location. The brace can then be designed and fabricated. The brace is then assembled with all of the modules and any required pads. As the hand heals, the individual modules can be removed from the brace and the patient can regain use of the hand. Eventually, only the damaged finger may need to be in a brace until the patient has fully recovered. Because the hand has many small components, it can be difficult to make and remove traditional hand casts. The inventive process greatly simplifies the recovery process because only one brace is required and the modules are simply removed as the patient heals.

Removing the modules at the designated time periods can be very important to the healing process. A joint that is left immobile for extended periods of time can become very stiff. Thus, it is important to make the joints active as soon as possible. The lower arm module 925 can continue to be worn to support the patient's arm until the injured bones completely heal. The inventive brace has many benefits over traditional cases. Since the modules are removed, new braces are not required. Since the braces modules are removable, the doctor can inspect the limb and the patient can clean the limb if necessary. The patient does not need to remain at the hospital after the injured limb is marked and photographed. A substantial amount of time is saved when each section is removed compared to having to periodically remove and replace the cast. The cross sections of each modular component of the brace can be adjusted as described to fit the patient's limb as the size changes. In particular, the cross sections can be reduced for improved fitting, if the limb shrinks due to atrophy.

In addition to being the proper dimensions, the brace or cast must also be strong enough for the required use. An ankle brace or walking cast may be required to support the user's weight and impact while running or jumping and an arm brace or cast must be able to withstand the normal use forces. In an embodiment, the strength of the brace or cast is determined by the geometry of the brace or cast components and the materials used to fabricate the components.

Suitable materials include plastic, specifically, high strength plastics such as high strength polyamides metals, but also alloys and composites such as carbon fiber in an epoxy binder. The brace can be created using a 3D printer in its final three dimensional form.

In another embodiment, markings on the skin can determine areas for padding of bony contours or areas for adding additional padding over time to maintain contour. Using this system, conforming pads can be printed by the same process to fit within the confines of "fitted regions" within the inner walls of the cast. An array of conforming surface pads of progressive thicknesses can be produced and provided to the health care provider with the initial cast. The inner conforming pads can be made of a softer flexible material that can be produced by additive manufacturing techniques.

The inner pads can have porosity and holes that matches the ventilation holes of the outer exoskeleton for improved ventilation. The inner pads can also have locking devices manufactured into the pads such that they snap into the correct location with the correct orientation. Alternatively, an adhesive can be used to attach the pads to the brace.

Because both the pads and brace are custom made, they may be marked with location indicators that can be text, color coding or symbols indicating where and possibly how the pad and brace should be attached to each other. For example, the text on the pad may state, "attach this pad to the upper back section of the brace by attaching the connector to hole A in the pad."

As the body heals, the lack of movement can result in atrophy which causes the body to shrink. Thus, the first set of pads may be thin. When the brace or cast with the original thin pads no longer fits properly, the thin pads are removed and replaced with thicker pads. The different sets of conforming pads can include the different thicknesses and can have interior surfaces that are expected to match the patient's limb as this surface geometry changes over time. These multiple sets of pads can be fabricated at the same time or alternatively, since the digital design for the pads is stored, additional pads can be fabricated from the stored pad designs at any time. When the pads are used in combination with the adjustable cross section brace, the compression of the pads can be controlled. When the brace can no longer properly support the limb, the pads can be removed and replaced with thicker pads.

Figure 36:
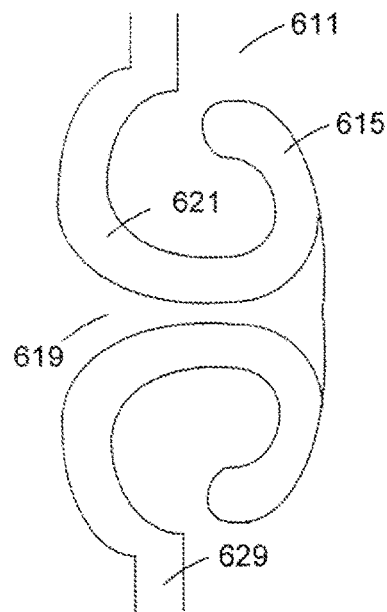
FIGS. 36-38 illustrate a side view of an embodiment of a single padding structure.

With reference to FIG. 36, a flowchart of the process steps for fabricating pads for a brace are illustrated. As discussed above, the patient's limb can be marked 661 with any type of marking device that can be photographed. The markings can indicate the location of the injury, edges of the brace, seams of the modular brace, seams of the brace pieces, sensitive areas, locations of stitches, and other body features. The patient's limb can be illuminated with IR or visible light in a pattern such as dots, lines, grids or any other plurality of light points 663. The limb can be photographed with IR and/or visible light cameras as described 665. From the photographic data, the surface data for the patient's limb can be obtained 667. In other embodiments the limb may not be illuminated with an IR or visible light pattern and the surface data can be obtained by the natural markings on the patient's skin.

The surface data can be used to design interior surfaces of a set of pads for a brace 669. In an embodiment, the pads can be fabricated through three dimensional printing and the padding can be placed in the brace shell. Once the three dimensional non-planar brace is assembled with the brace shell and pads, the brace can be worn by the patient to protect the limb 673. As the limb changes due to healing and/or atrophy, the surface of the limb can change 675. As discussed, the brace shell may be adjustable and tightened to provide a better fit, though no fastening device is required to hold its conformation around the limb. In other embodiments, the brace shell may not be adjustable, and if the limb gets smaller in size, the fit of the brace may need to be adjusted. The described process can be repeated to fabricate a new set of pads based upon new photographs of the patient's limb. The patient can simply remove the prior set of pads from the brace shell and install the new pads. This process can be repeated until the patient no longer needs a brace.

Figure 37:
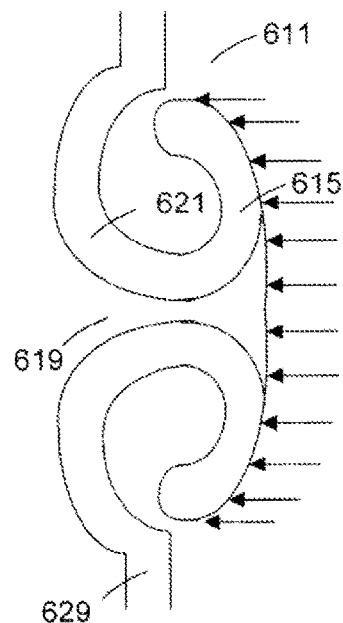
Figure 38:
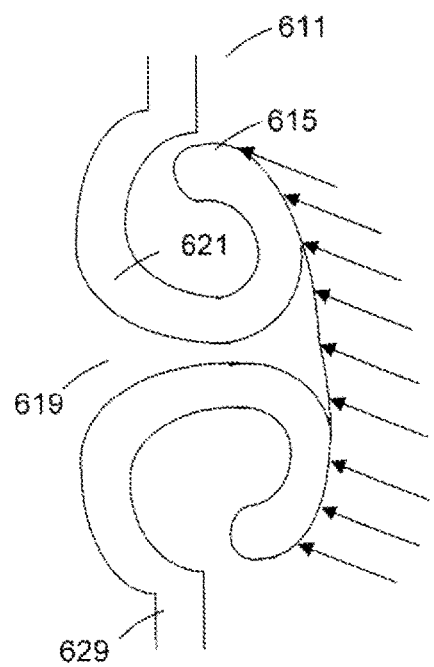
Figure 39:
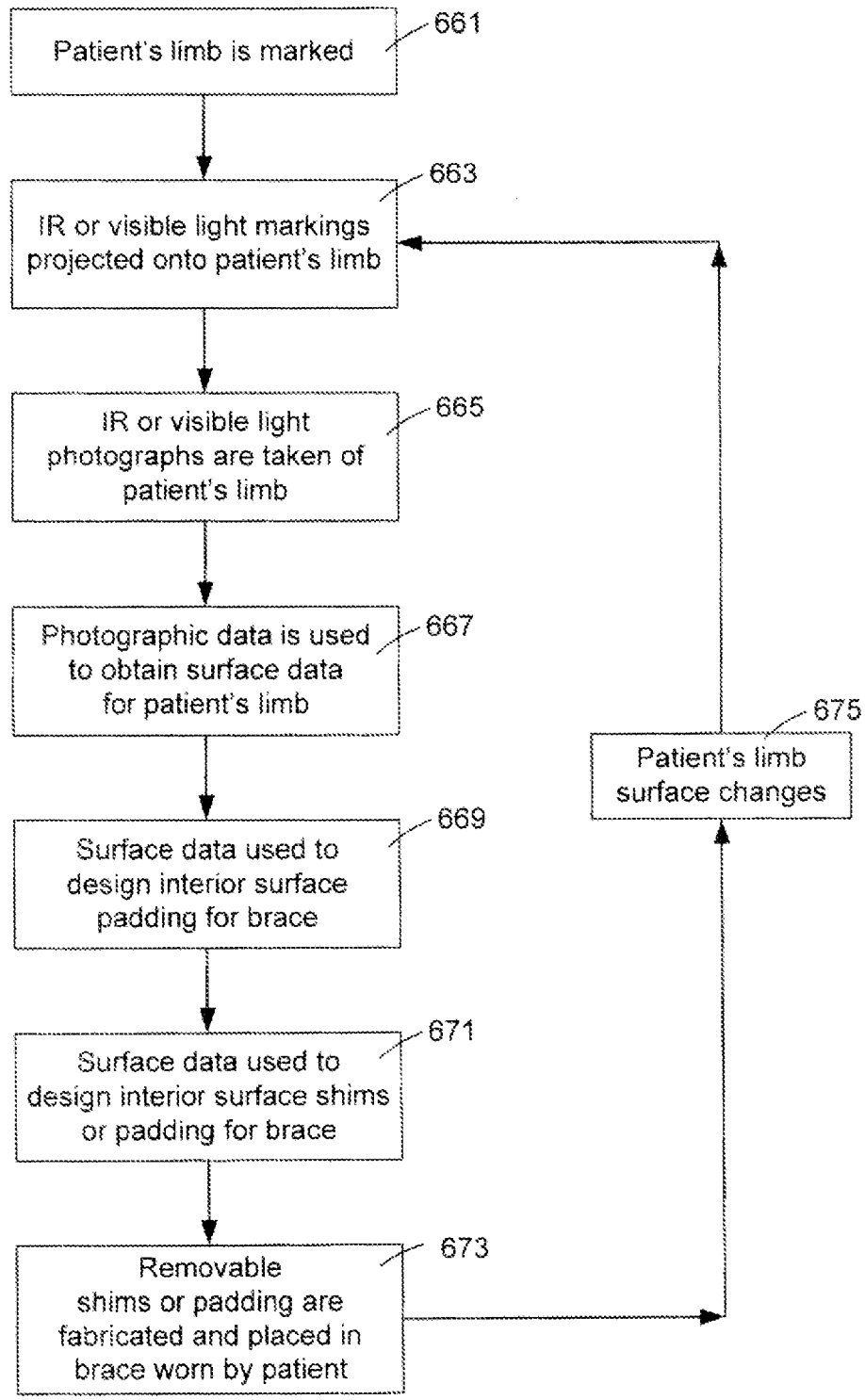
FIG. 39 is a flow chart of a shim or padding design and fabrication for a brace.

With reference to FIGS. 37-39, another feature that can be designed into the brace is a dense grid of individually suspended contact pads 611 which involves each pad 611 being 'hollow', giving it the shape of a torroid. This allows contact 'rings' 615 to contact the skin, each one with a ventilation hole 619 at the center. This gives improved airflow to the skin. The 'doughnut' shape of it makes window edema less likely, since there are no hard edges to press against the skin to disturb the blood flow. And the relatively large contact pad 611 area will likely increase the comfort against the skin. Air will also flow around each of the contact pads 611, and can be evacuated through a perforation pattern through the outer wall. This will increase comfort to the user and cool the surface skin temperature.

Because each of the contact pads 611 may be created as an individual revolved 'cell', it can be created so that a 'well' exists around each of the pad's 'stocks'. Beyond the 'well', the wall thickness grows, since the thick parts of the cells intersect adjacent cells. This allows a relatively strong structure to be created that is flexible where desired (around the stocks of each pad), yet strong where desired (in between each stock). Both strength and compliance is met in a single surface.

For dynamic braces, these contact pad 611 constructs can be produced as a coherent volume of attached structures, or for more dynamic braces, the contact pads 611 may be printed as discrete elements in continuity with the outer exoskeleton and ventilation pattern, but whereby the contact pads 611 and support structure exclusive of the exoskeleton are not in contact. Such a construct would allow for differing motions in select regions of the brace without any impact on the mechanical properties due to the contact pads.

The pads 611 illustrated in FIGS. 37-39 are part of the inner surface of the brace. Each pad 611 is flexible and movable in compression as well as horizontal movement. In an embodiment, the pads 611 each have a contact portion 615 and a stem 621 that is coupled to a frame. When the pad 611 is compressed against a portion of the patient's body, for example when the brace is worn by the patient, the contact portion 615 is compressed against the stem 621 which is compressed against the frame 629. The stem 621 can be much narrower than the contact portion and bendable. When the contact portion 615 of the pad 611 moves horizontally, the stem 621 will bend in response to the pad 611 movement. The stem 621 is also coupled to the frame 629 in such a way that the stem 621 can move in a perpendicular direction relative to the plane of the frame 629. Thus, the pad 611 can move in response to any perpendicular compression of the pad 611 against the frame of the brace. In an embodiment, a portion or the entire interior surfaces of the brace can include the described pads 611. The pads 611 used in a brace can all be identical or each can have a different design characteristics. For example, the pads 611 located over harder surfaces such as bones under the skin can have flexible pads 611 that allow for comfortable movement of the bones and/or joints. In contract, the pads 611 that are located over softer areas of the body can have stiffer constitution since the soft areas may not require as much padding. FIG. 36 illustrates a cross section of an example of a single pad 611 element. FIG. 37 illustrates the pad 611 in direct compression and FIG. 38 illustrates the pad 611 in diagonal compression. In the compressed illustrations, the stem 621 bends in response to the pressure applied to the pad 611.

In other embodiments, different flexible pad designs can be used including non-circular surfaces, different spring stems and different ventilation mechanisms. The hardness or softness of the pads can be quantified by the spring rate of the stem against the frame and the contact area of the pad. A pad with a large contact area and a low spring rate will be very soft. In contrast, a pad with a small contact area and a high spring rate will be a harder pad. The equation quantifying the hardness or softness of the pads is (pad surface area)×(stem spring rate)=X. For example, if the pad area is 1 square inch and the spring rate is 10 lb per inch, when the pad is compressed ¼ inch into the frame, the force will be 2.5 lbs per square inch. If the pad is compressed ½ inch into the frame the force will be 5 lbs per square inch. The dynamic hardness/softness characteristics of each of the pads can be individually designed into the brace. The pad areas can range from about ¼ square inch to about 5 square inches and the spring rate of the stem can range from about 0.01 lb/in to about 100 lb/in.

Figure 23:
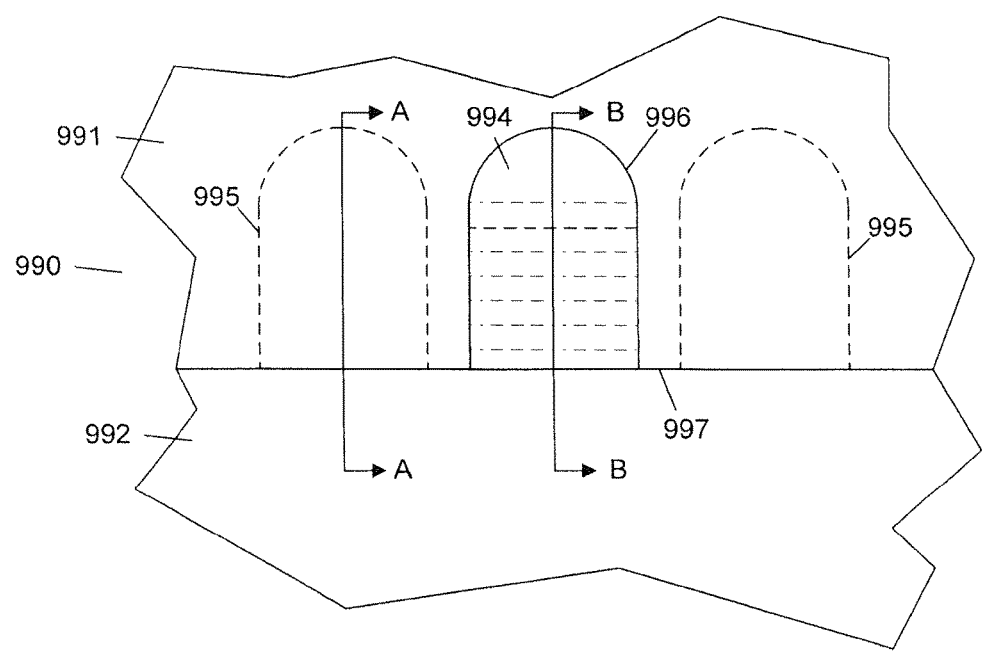
FIGS. 23-35 illustrate an embodiment of an adjustable fastener used to connect different sections of a modular brace along a seam.
Figure 24:
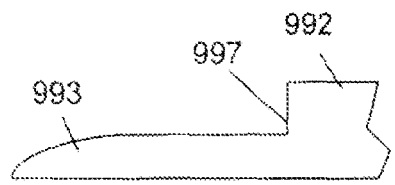

With reference to FIGS. 23 and 24, a top view and a bottom view of an adjustable fastener 990 that can be used to connect a first section 991 to a second section 992 of a brace along a seam 997 and alter a cross section of the brace. In this example, the seam 997 is illustrated as being a straight line. In other embodiments, the seam 997 can be curved. In an embodiment, the seam 997 can be perpendicular to the inner and outer surfaces of the first section 991. In another embodiment, the seam edge of the first section 991 can be a concave curve and the seam edge of the second section 992 can be a convex curve so that compressive forces can be transferred across the seam 997 without shifts the alignment of the first section 991 and a second section 992.

Figure 22:
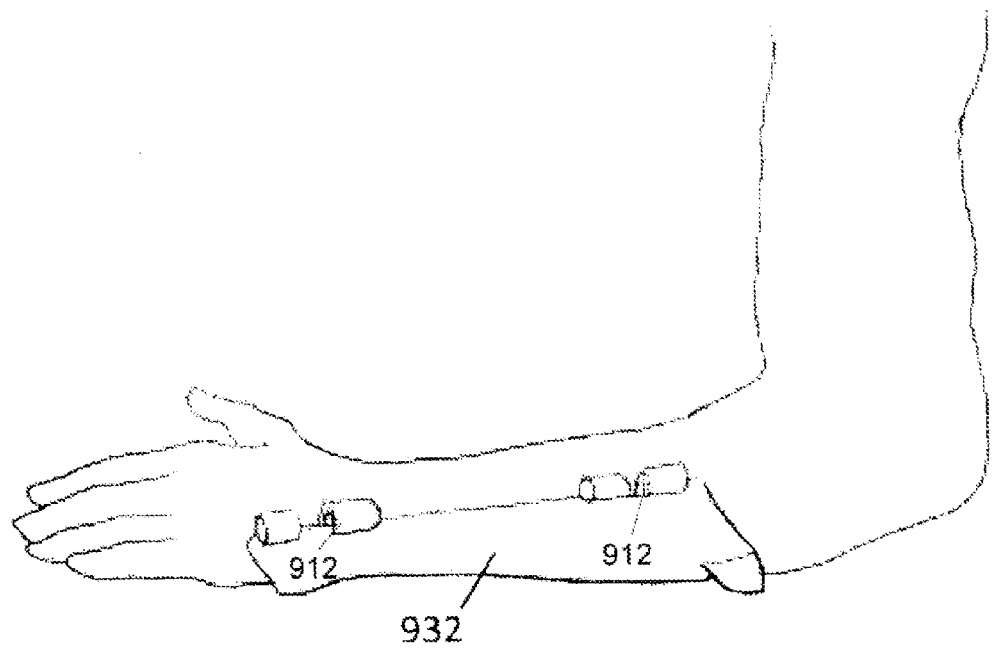
Figure 25:
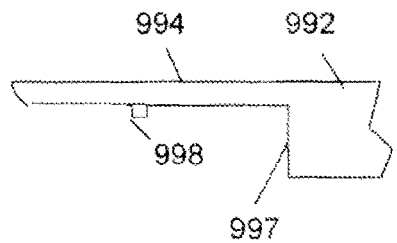
Figure 26:
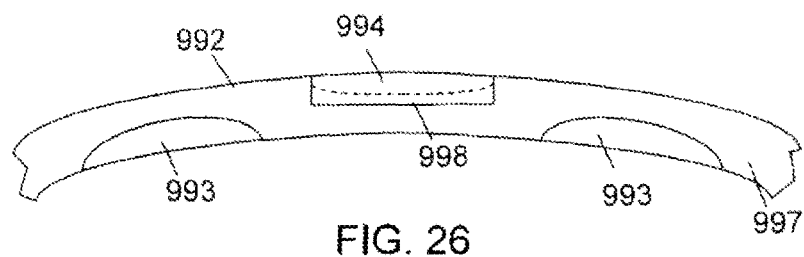
Figure 27:
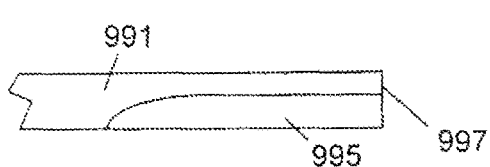
Figure 28:
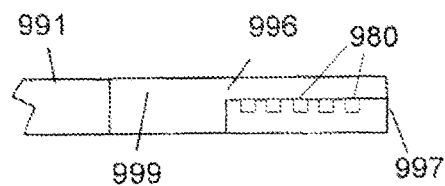
Figure 29:
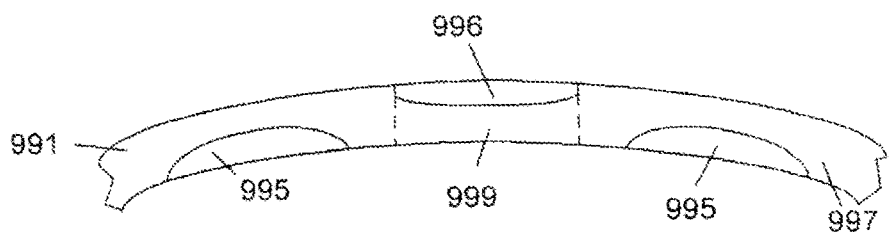

In an embodiment, the adjustable fastener 990 can include a plurality of tabs 993, 994 that extend from the second section 992 and grooves 995, 996 that are formed in the first section 991. Details of an embodiment of the tabs 993, 994 are illustrated in FIGS. 24-26. FIG. 24 illustrates a cross section side view A-A of tab 993 as shown in FIGS. 22 and 23. The front end of the tab 993 is tapered and the bottom surface can be the interior or exterior surface of the brace. FIG. 25 illustrates a cross section view B-B of tab 994 which has a front end that is tapered and a latch 998 that locks the adjustable fastener 990 together. The top surface of the tab 994 can be the interior or exterior surface of the brace. With reference to FIG. 26, a front view of the tabs 993 and 994 is illustrated. The cross section of the second section 992 can be curved and the lower surfaces of the tabs 993 can match the curvature of the lower surface of the second section 992 and the upper surface can be a convex surface. The tab 994 can also have a curved upper surface that matches the upper surface of the second section 992. The tab 998 can be a locking protrusion that engages one or a plurality of recesses 980 formed across the groove 996. Details of the grooves 995, 996 are illustrated with reference to FIGS. 27-29. FIG. 27 illustrates a cross section side view A-A of the groove 995 as shown in FIGS. 22 and 23. The groove 995 in the first section 991 includes a concave surface formed in the lower surface of the first section 991 that extends inward from the seam 997. FIG. 28 illustrates an embodiment of a cross section side view B-B of the groove 996 as shown in FIGS. 22 and 23. The groove 996 can be formed in the upper surface of the first section 991 and extend inward from the seam 997. The groove 996 can include a plurality of recesses 980 that extend across the groove 996 and the groove 996 may be connected to a through hole section 999 that extends between the upper and lower surfaces of the first section 991. FIG. 29 is a front view of the grooves 995, 996 which shows the curvatures of the first section 991.

Figure 30:
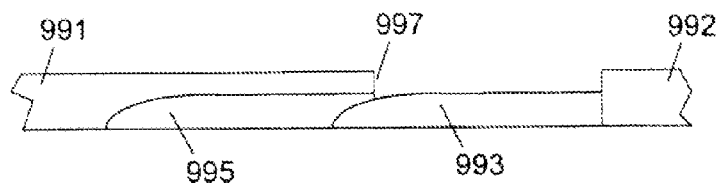
Figure 31:
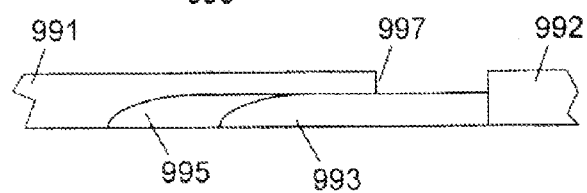
Figure 32:
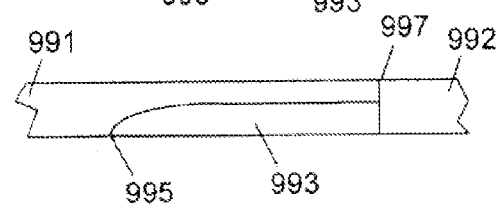
Figure 33:
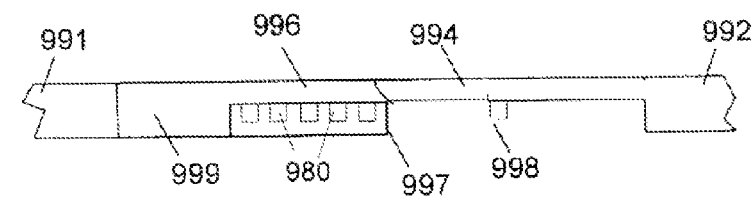
Figure 34:
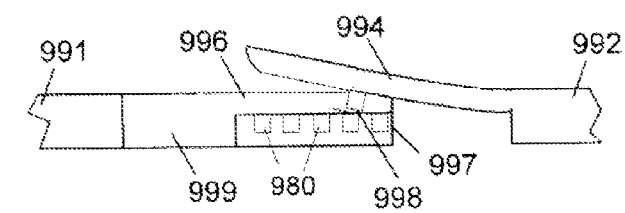
Figure 35:
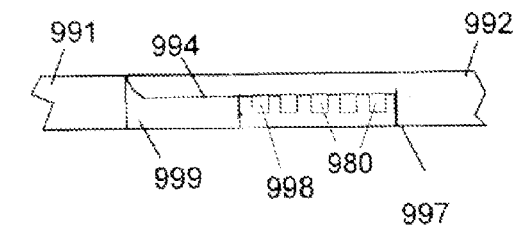

With reference to FIGS. 30-35, cross section side views of the tabs 994, 995 being inserted into the grooves 995, 996 to connect the first section 991 and the second section 992 of the brace are illustrated. FIG. 30 illustrates the tab 993 entering the groove 995. FIG. 31 shows the tab 993 partially in the groove 995 and FIG. 32 shows the tab 993 fully inserted into the groove 995. The bottom of the tab 993 remains flush with the bottom of the first section 991. When fully inserted, the first section 991 is coupled to the second section 992 along the seam 997. FIG. 33 shows the tab 994 entering the groove 996. FIG. 34 shows the tab 994 partially in the groove 996 and deflected upward. FIG. 35 shows the tab 994 fully inserted into the groove 996 with the protrusion 998 within one of the recesses 980 to lock the tab in place. In this embodiment, the first section 991 and the second section 992 can only be separated by deflecting the tab 994 to remove the protrusion 998 from the recesses 980. The connector illustrated in FIGS. 23-35 can be an integrated curved design that conforms to any curved surface of the patient's surface topography and can provide a rigid connection between the first section 991 and the second section 992.

Figure 40:
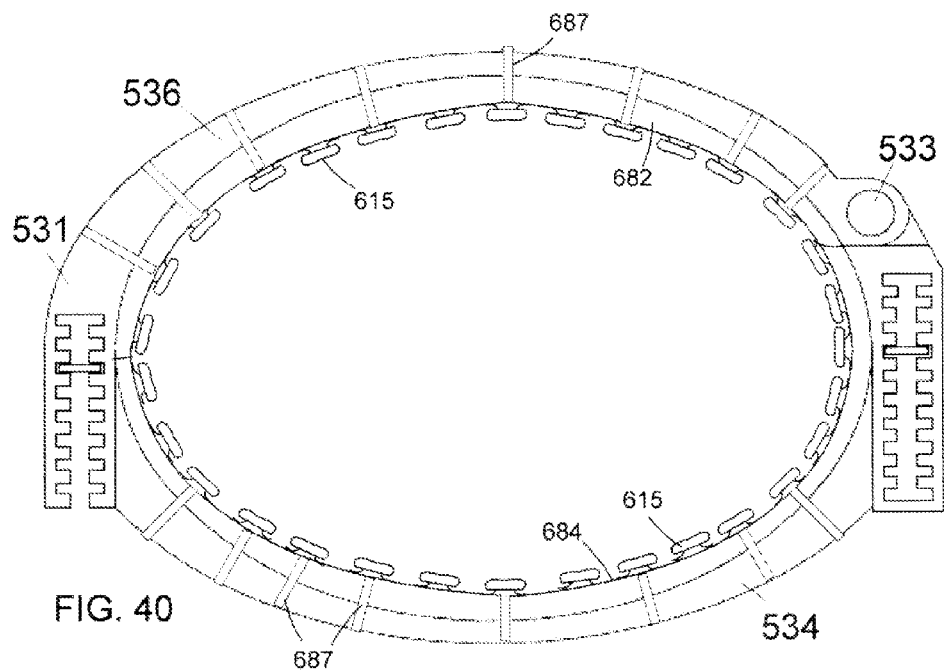
FIGS. 40-41 illustrate an embodiment of a padding structure that can be a removable interior surface of a brace.
Figure 41:
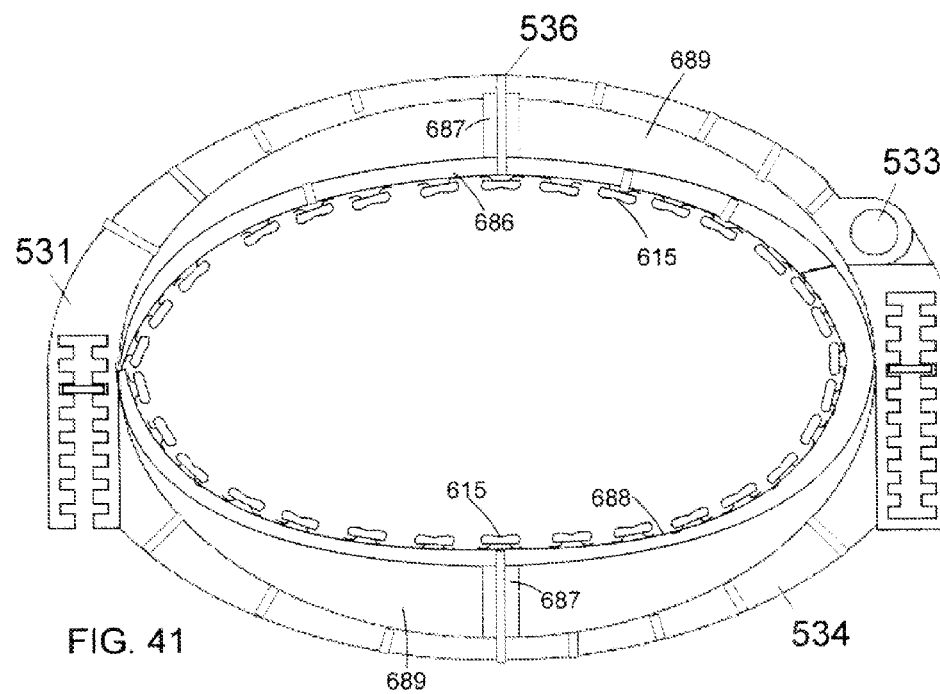

As discussed in some embodiments, the brace can have a plurality of pad sets that can be placed within a brace shell. As the surface of the limb changes, the initial pad can be removed and other pad sets can be installed so that the brace can properly support the limb. With reference to FIGS. 40 and 41, cross sections of a brace having different interior padding sets are illustrated. The brace can have an upper portion 536 that is coupled to a lower portion 534 by a hinge 533 on one edge and an adjustable coupling 531 on the opposite edge, with each portion inherently having inner surface shapes that correspond to a digital representation of the limb. In other embodiments, the brace can also include non adjustable fasteners rather than adjustable fasteners. In FIG. 40, the thickness of the padding set 682, 684 is thinner than the padding set illustrated in FIG. 41. When a patient injures his or her limb, the initial cross section of the limb can be large due to swelling. Thus, the interior cross section of the brace in FIG. 40 can correspond to the initial larger cross section surfaces. In contrast, in FIG. 41, the interior volume is smaller because the padding set 686, 688 is thicker.

In an embodiment the interior surface of the padding sets 682, 684, 686, 688 include compressible pads 611 that can be the same or similar to the pads illustrated in FIGS. 37-39. These pads 611 can be formed with surfaces that correspond to the surface data of the patient's limb. The pads 611 can be formed with or attached to each of the padding sets 682, 684, 686, 688. As discussed above with reference to FIGS. 37-39, the pads 611 can provide ventilation so that the patient's limb is exposed to ambient air through the open spaces between the pads 611 as well as the holes within the pads 611. In an embodiment the padding sets 682, 684, 686, 688 can also include additional fenestrations to improve ventilation. In an embodiment, the brace can include connectors 687 that releasably connect the padding sets 682, 684, 686, 688 to fenestrations or other features of the upper portion 536 and the lower portion 534 of the brace. The connectors can be tubular structures that allow air to pass from the outer portion of the brace through the pads 611 to the limb of the patient. In an embodiment, open spaces 689 can exist between the padding set 686, 688 and the upper portion 536 and the lower portion 534 of the brace. These open spaces 689 can provide ventilation to allow air to flow through the fenestrations in the padding set 686, 688 and the upper portion 536 and the lower portion 534 of the brace.

After the brace or device is designed with the adjustable couplings incorporated, the brace design data can be transmitted to a three dimensional fabrication machine that constructs the three dimensional non-planar brace structure(s). In an embodiment, the three dimensional fabrication machine is rapid prototyping, rapid manufacturing, layered manufacturing, 3D printing, laser sintering, and electron beam melting (EBM), fused material deposition (FDM), CNC, etc. The fabrication machine produces a three dimensional single or multiple piece non-planar structure that can be plastic, metal or a mix of different materials. In order to efficiently produce the described devices, it can be desirable to simultaneously produce as many component parts as possible. Many fabrication machines can produce parts fitting within a specific volume in a predetermined period of time. For example, a brace can fit around the torso of a patient and have a large space in the center. This brace can be made, but it will only make one device. In order to improve the efficiency, the brace can be designed as multiple pieces that are later coupled or fused together. Rather than making a single brace with the large open center area, the described fabrication methods can be used to simultaneously produce components for two or more braces that occupy the same specific volume as a single piece brace. The cost of fabrication using a three dimensional fabrication machine can be proportional to the amount of time required to print the components rather than the raw material costs. The print time can be minimized by placing as many component cross sections into the print area as possible. If a back or limb brace normally has a large open center area the print cost efficiency can be poor. However, if the brace is a modular design, the modular section pieces can be fabricated in a more efficient manner. For example, multiple modular section pieces can be fabricated simultaneously with the convex surfaces of a first section piece adjacent to concave surfaces of another section piece. By laying out the components in an efficient production manner for fabrication by an additive material machine, the cost of fabrication can be significantly reduced. The components can then be assembled and coupled or fused together to form the three dimensional non-planar brace structure. In an embodiment, the inner surface of the brace can be manufactured with a high resolution so that the inner surface is very smooth, eliminating the need for a layer of a soft, breathable material in contact with the skin.

After the brace shell has been formed, additional processing can be performed on the inner surface to increase the smoothness. The inner surface can be tumbled, sanded, polished, or other processes can be used to create the smooth inner surfaces of the brace. These processes can be performed by hand or by a machine. In other embodiments, a filler material can be deposited on the inner surface of the brace shell to create a smooth surface. For example, the inner surface may be painted and the paint may fill the uneven surfaces and dry to a smooth surface. Alternatively, the inner surface can be heated to cause the brace material to reflow and create a smooth inner surface.

The use of a photographic process has many advantages over other surface scanning technologies such as laser scanning. The process for transposing the locations of features from the patient to the brace or device is simplified because the doctor can apply location marks to the patient directly or on a form fitting covering. Thus, the locations of the features are much more likely to be accurately placed on the final product. The equipment costs are also reduced because the digital cameras, computers and electronic memory are inexpensive. The photographic equipment is also portable, so it can be easily transported to patient's location. The digital data can then be transmitted electronically to a fabrication machine located at a guild. Alternatively, the digital device data can be recorded onto a disk and transmitted to the fabrication machine.

The present disclosure, in various embodiments, includes components, methods, processes, systems and/or apparatus substantially as depicted and described herein, including various embodiments, subcombinations, and subsets thereof. Those of skill in the art will understand how to make and use the present disclosure after understanding the present disclosure. The present disclosure, in various embodiments, includes providing devices and processes in the absence of items not depicted and/or described herein or in various embodiments hereof, including in the absence of such items as may have been used in previous devices or processes, e.g., for improving performance, achieving ease and/or reducing cost of implementation. Rather, as the flowing claims reflect, inventive aspects lie in less than all features of any single foregoing disclosed embodiment.

What is claimed is:

1. An adjustable brace comprising:
    a first rigid portion for supporting a first surface of a limb;
    an adjustable portion that is coupled to the first rigid portion for supporting an injured portion of the limb that is opposite the first surface of the limb; and
    adjustable couplings having a first plurality of fingers attached to the first rigid portion and a second plurality of fingers attached to the adjustable portion wherein the first plurality of fingers attached to the first rigid portion overlap and are offset from the second plurality of fingers attached to the adjustable portion;
    a locking mechanism for securing an elongated structure within a plurality of slots or holes formed in the first plurality of fingers attached to the first rigid portion and the second plurality of fingers attached to the adjustable portion to prevent a patient from adjusting the adjustable brace;
    wherein the first rigid portion inherently holds inner surfaces of the first rigid portion in a first shape that corresponds to a digital representation of the first surface of the limb and inner surfaces of the adjustable portion are adjustable to fit closely against the second surface of the limb in a swollen state and adjustable to fit closely against the second surface of the limb in a normal unswollen state and the first rigid portion and the adjustable portion are made entirely of a plastic material.

2. The adjustable brace of claim 1 wherein the adjustable couplings include a plurality of slots or holes.

3. The adjustable brace of claim 2 wherein the plurality of slots or holes are adjacent to each other.

4. The adjustable brace of claim 2 further comprising:
    an elongated structure inserted within one or more of the plurality of slots or holes of the adjustable couplings.

5. The adjustable brace of claim 1 wherein the adjustable couplings are adjustable to alter cross sections of the adjustable brace.

6. The adjustable brace of claim 1 wherein the adjustable brace has a variable cross section.

7. An adjustable brace comprising:
a first rigid portion for supporting a first surface of a limb;
an adjustable portion that is coupled to the first rigid portion for supporting a second surface of the limb that is opposite the first surface of the limb; and
adjustable couplings having a first plurality of fingers attached to the first rigid portion and a second plurality of fingers attached to the adjustable portion wherein the first plurality of fingers attached to the first rigid portion overlap and are offset from the second plurality of fingers attached to the adjustable portion;
wherein the first rigid portion inherently holds inner surfaces of the first rigid portion in a first shape that corresponds to a digital representation of the first surface of the limb and the adjustable portion inherently holds inner surfaces of the adjustable portion in a second shape that corresponds to a digital representation of the second surface of the limb and the first rigid portion and the adjustable portion are made entirely of a plastic material;
a locking mechanism for securing an elongated structure within a plurality of slots or holes formed in the first plurality of fingers attached to the first rigid portion and the second plurality of fingers attached to the adjustable portion to prevent a patient from adjusting the adjustable brace.

8. The adjustable brace of claim 7 further comprising:
a hinge attached to a second edge of the first rigid portion opposite the first edge for coupling the second edge of the first rigid portion to the adjustable portion.

9. The adjustable brace of claim 7 wherein the adjustable portion is adjustable to alter cross sections of the brace.

10. The adjustable brace of claim 7 wherein the adjustable portion can bend or twist to accommodate changes in a cross section of the adjustable brace.

11. The adjustable brace of claim 7 wherein for the adjustable couplings, distances between a hinge and each of a plurality of slots or holes formed in the first plurality of fingers and the second plurality of fingers are substantially the same.

12. An adjustable brace comprising:
a first rigid portion for supporting a first surface of a limb;
an adjustable portion that is coupled to the first rigid portion for supporting a second surface of the limb that is opposite the first surface of the limb; and
adjustable couplings having a first finger attached to the first rigid portion and a second finger attached to the adjustable portion wherein the first finger overlaps and is offset from the second finger;
a locking mechanism for securing an elongated structure within a plurality of slots or holes formed in the first finger and the second finger to prevent a patient from adjusting the adjustable brace;
wherein the first rigid portion inherently holds inner surfaces of the first rigid portion in a first shape that corresponds to a digital representation of the first surface of the limb and the adjustable portion inherently holds inner surfaces of the adjustable portion in a second shape that corresponds to a digital representation of the second surface of the limb and the first rigid portion and the adjustable portion are made entirely of a plastic material.

13. The adjustable brace of claim 12 wherein the adjustable couplings are attached to an first edge of the first rigid portion and a second edge of the adjustable portion and the adjustable couplings includes a first plurality of slots or holes.

* * * * *